United States Patent
Daniell

(10) Patent No.: US 11,007,247 B2
(45) Date of Patent: May 18, 2021

(54) COMPOSITIONS AND METHODS FOR DELIVERY OF BIOENCAPSULATED PROTEINS ACROSS BLOOD-BRAIN AND RETINAL BARRIERS

(71) Applicants: Henry Daniell, Media, PA (US); THE TRUSTEES OF THE UNIVERSITY OF PENNSYLVANIA, Philadelphia, PA (US)

(72) Inventor: Henry Daniell, Media, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 0 days.

(21) Appl. No.: 15/038,068

(22) PCT Filed: Nov. 21, 2014

(86) PCT No.: PCT/US2014/066851
§ 371 (c)(1),
(2) Date: May 20, 2016

(87) PCT Pub. No.: WO2015/077578
PCT Pub. Date: May 28, 2015

(65) Prior Publication Data
US 2016/0367629 A1 Dec. 22, 2016

Related U.S. Application Data

(60) Provisional application No. 61/907,368, filed on Nov. 21, 2013.

(51) Int. Cl.
| | |
|---|---|
| *A61K 38/17* | (2006.01) |
| *C07K 14/47* | (2006.01) |
| *A61K 38/16* | (2006.01) |
| *A61K 47/64* | (2017.01) |
| *A61K 47/68* | (2017.01) |
| *A61K 9/00* | (2006.01) |
| *A61K 9/19* | (2006.01) |
| *A61K 9/50* | (2006.01) |
| *C07K 14/28* | (2006.01) |
| *C12N 15/82* | (2006.01) |

(52) U.S. Cl.
CPC ........ *A61K 38/1709* (2013.01); *A61K 9/0053* (2013.01); *A61K 9/19* (2013.01); *A61K 9/5068* (2013.01); *A61K 38/164* (2013.01); *A61K 38/17* (2013.01); *A61K 47/6415* (2017.08); *A61K 47/6811* (2017.08); *C07K 14/28* (2013.01); *C07K 14/4713* (2013.01); *C12N 15/8257* (2013.01); *C07K 2319/00* (2013.01); *C07K 2319/55* (2013.01); *Y02A 50/30* (2018.01)

(58) Field of Classification Search
CPC .. A61K 38/1709; A61K 38/17; A61K 38/164; A61K 47/6415; A61K 47/6811; A61K 9/0053; A61K 9/19; A61K 9/5068; C07K 14/28; C07K 14/4713; C07K 2319/00; C07K 2319/55
See application file for complete search history.

(56) References Cited

U.S. PATENT DOCUMENTS

2010/0266640 A1* 10/2010 Daniell ............... A61K 39/015
424/261.1

OTHER PUBLICATIONS

Sun et al. Oral administration of cholera toxin B subunit conjugated to myelin basic protein protects against experimental autoimmune encephalomyelitis by inducing transforming growth factor-beta-secreting cells and suppressing chemokine expression. Int Immunol. Oct. 2000;12(10):1449-57.*
Stevenson. Characterization of protein and peptide stability and solubility in non-aqueous solvents. Curr Pharm Biotechnol. Sep. 2000;1(2):165-82.*
Newton et al. Neurological manifestations of falciparum malaria. Ann Neurol. Jun. 1998;43(6):695-702.*
Boggs, J.M., "Myelin basic protein: a multifunctional protein", Cell. Mol. Life Sci., 63: 1945-1961 (2006).
Bowman, G.L. et al., "Blood-brain barrier impairment in Alzheimer disease: Stability and functional significance", Neurology, 68(21): 1809-1814 (2007).
Bucolo, Claudio et al., "Ocular drug delivery: a clue from nanotechnology", Frontiers in Pharmacology, 3: 188 (2012).
Fang, Yu et al., "Characterization of Cholera Toxin B Subunit-Induced Ca2+ Influex in Neuroblastoma Cells: Evidence for a Voltage-Independent GM1 Ganglioside-Associated Ca2+ Channel", Journal of Neuroscience Research, 69: 669-680 (2002).
Farlow, Martin R. et al., "Effectiveness and Tolerability of High-Dose (23 mg/d) Versus Standard-Dose (10 mg/d) Donepezil in Moderate to Severe Alzheimer's Disease: A 24-Week, Randomized, Double-Blind Study", Clinical Therapeutics, 32(7): 1234-1251 (2010).
Gabathuler, Reinhard, "Approaches to transport therapeutic drugs across the blood-brain barrier to treat brain diseases", Neurobiology of Disease, 37: 48-57 (2010).
Georgieva, Julia V. et al., "Peptide-Mediated Blood-Brain Transport of Polymersomes", Angew. Chem. Int. Ed., 51: 8339-8342 (2012).
Goldstein, Lee E. et al., "Cytosolic B-amyloid deposition and supranuclear cataracts in lenses from people with Alzheimer's disease", The Lancet, 361: 1258-1265 (2003).
Guo, L. et al., "Alzheimer's Disease and Retinal Neurodegeneration", Current Alzheimer Research, 7 (2010).
Guo, L. et al., "Targeting amyloid-B in glaucoma treatment", PNAS, 104(33): 13444-13449 (2007).

(Continued)

*Primary Examiner* — Gregory S Emch
(74) *Attorney, Agent, or Firm* — Kathleen D. Rigaut; Howson & Howson LLP

(57) ABSTRACT

Compositions and methods effective to provide therapeutic benefit for disorders of the central nervous system via oral or systemic delivery of therapeutic proteins produced in plastids are disclosed.

2 Claims, 13 Drawing Sheets

(56) References Cited

OTHER PUBLICATIONS

Hoos, Michael D. et al., "Myelin basic protein binds to and inhibits the fibrillar assembly of AB42 in-vitro", Biochemistry, 48(22): 4720-4727 (2009).

Janciauskiene, Sabina et al., "Alzheimer's peptide: A possible link between glaucoma, exfoliation syndrome and Alzheimer's disease", Acta Ophthalmol. Scand., 79: 328-329 (2001).

Janciauskiene, Sabina et al., "Alzheimer's peptide and serine proteinase inhibitors in glaucoma and exfoliation syndrome", Documenta Ophthalmologica, 106: 215-223 (2003).

Lee, Andrew G. et al., "Neuro-ophthalmic Findings in the Visual Variant of Alzheimer's Disease", Ophthalmology, 111: 376-381 (2004).

Lippmann, Ethan S. et al., "Derivation of blood-brain barrier endothelial cells from human pluripotent stem cells", Nature Biotechnology, 30(8): 783-791 (2012).

Luissint, Anny-Claude et al., "Tight junctions at the blood brain barrier: physiological architecture and disease-associated dysregulation", Fluids and Barriers of the CNS, 9: 23 (2012).

Masters, Colin L. et al., "Biochemistry of Amyloid B-Protein and Amyloid Deposits in Alzheimer's Disease", Cold Spring Harb Perspect Med, 2 (2012).

Mattson, Mark P., "Pathways towards and away from Alzheimer's disease", Nature, 430: 631-639 (2004).

Mitew, Stanislaw et al., "Focal demyelination in Alzheimer's disease and transgenic mouse models", Acta Neuropathol., 119: 567-577 (2010).

Pardridge, William M., "Drug transport across the blood-brain barrier", Journal of Cerebral Blood Flow & Metabolism, 32: 1959-1972 (2012).

Rizzolo, Lawrence J. et al., "Integration of tight junctions and claudins with the barrier functions of the retinal pigment epithelium", Progress in Retinal and Eye Research, 30: 296-323 (2011).

Sanchez, J. et al., "Cholera toxin structure, gene regulation and pathophysiological and immunological aspects", Cell. Mol. Sci., 65: 1347-1360 (2008).

Tabaton, M. et al., "The molecular link between B- and y-secretase activity on the amyloid B precursor protein", Cell. Mol. Life Sci., 64: 2211-2218 (2007).

Taylor, J. Paul et al., "Toxic Proteins in Neurodegenerative Diseases", Science, 296: 1991-1995 (2002).

Thrimawithana, Thilini Rasika et al., "Drug delivery to the posterior segment of the eye", Drug Discovery Today, 16: 270-277 (2011).

Tsai, Julia et al., "Fibrillar amyloid deposition leads to local synaptic abnormalities and breakage of neuronal branches", Nature Neuroscience, 7(11): 1181-1183 (2004).

Yoshida, Takeshi et al., "The potential role of amyloid B in the pathogenesis of age-related macular degeneration", The Journal of Clinical Investigation, 115(10): 2793-2800 (2005).

Alzheimer's Disease International, World Alzheimer Report 2010, "The Global Economic Impact of Dementia".

Alzheimer's Association, 2011 Alzheimer's Disease Facts and Figures, Overview of Alzheimer's Disease, pp. 1-63.

\* cited by examiner

COMPOSITIONS AND METHODS FOR DELIVERY OF BIOENCAPSULATED PROTEINS ACROSS BLOOD-BRAIN AND RETINAL BARRIERS

This application is a § 371 of International Application No. PCT/US2014/066851, filed Nov. 21, 2014, which claims the benefit of U.S. Provisional Application No. 61/907,368, filed Nov. 21, 2013, the contents being incorporated herein by reference as though set forth in full.

STATEMENT OF GOVERNMENT INTEREST

This invention was made with government support under grant numbers HL107904 and HL109442 awarded by the National Institutes of Health. The government has certain rights in the invention.

FIELD OF THE INVENTION

This invention relates to the fields of plastid transformation and recombinant production of beneficial therapeutic products. More specifically, the invention provides compositions and methods for efficacious delivery of therapeutic molecules of interest across the blood brain barrier in patients in need thereof.

BACKGROUND OF THE INVENTION

Several publications and patent documents are cited throughout the specification in order to describe the state of the art to which this invention pertains. Each of these citations is incorporated herein by reference as though set forth in full.

Drug delivery of biologics from bloodstream to the brain across the blood brain barrier (BBB) has long been a major challenge to treat neuronal degenerative disorders (1-3). Invasive approach to bypass the BBB includes intracerebroventricular infusion, convection-enhanced delivery or microchip systems to release such therapeutics. However, these strategies are neither efficient to deliver optimal concentrations of drug to the brain parenchyma, nor patient friendly, enhancing tumor dissemination (4). Modification of chemical properties of drugs can facilitate penetration across BBB but often results in losing the desired CNS activity (2, 4). Although the transcytosis mechanism (4) across polarized endothelial cells at BBB is not clear, selection of high affinity GM1 binding ligands, like the cholera toxin B subunit (CTB) should address the process of transcytosis across BBB. However, no attention has been paid for developing oral drug delivery systems to address neurological diseases.

Likewise ocular drug delivery, particularly to the posterior segment of the eye, is also a major challenge due to several anatomical and physiological constraints of the eye (5-6). Topically administered drug cannot reach the retina and vitreous cavity because of the ocular surface barriers, which include cornea epithelium, stroma, and endothelial layers, and continuous tear drainage, frontward flow of aqueous humor, and surrounding blood circulations, all limiting the penetration of topically administered drug. Although intravenous administration is extensively used for delivering drugs to the posterior part of the eye, ocular pharmacologists face major obstacles (7) like retinal detachment, endophthalmitis, and high intraocular pressure through this accessible route.

Alzheimer's disease (AD) is the most common neurodegenerative disease and the sixth leading cause of death in the United States, affecting an estimated 5.4 million Americans and 36 million people globally (8), with treatment cost exceeding $600 billion, posing a major healthcare challenge. By the year 2050, it is estimated that the incidence of AD will reach >100 million patients worldwide (9). One of the major pathological hallmarks of AD is the deposition of amyloid beta 42 ($A\beta_{42}$) as extracellular neuronal plaques (10). The $A\beta_{42}$ peptide is produced by the sequential cleavage of the Amyloid Precursor Protein (APP) within lipid rafts by endo-proteolytic enzymes β and γ secretase, respectively (11). Following cleavage of APP, Aβ fragments of different lengths $A\beta_{42}$, $A\beta_{38}$, and even $A\beta_{46}$ are produced, with the predominant form being $A\beta_{40}$ (12). Although the $A\beta_{42}$ is a minor species, it has a greater propensity to aggregate and form plaques. This leads to a detrimental loss of synaptic structural integrity/communication between axon and dendrites, contributing to cognitive dysfunction leading to neuronal degeneration (13). Current FDA approved pharmaco-therapies provide some symptomatic benefits but they don't prevent disease progression (14).

Furthermore, visual abnormalities are also prevalent among AD patients. Visual disturbances in AD patients include impaired motion and depth perception, spatial contrast sensitivity and color recognition (15), associated with degeneration and loss of retinal ganglion cells (RGC) and reduction of retinal nerve fibers (16). Aβ deposition in the retina appeared to be associated with RGC apoptosis and retinal structural and functional impairment (16). In addition, Aβ deposits have been reported in glaucomatous optic nerve heads, drusen of age-related macular degeneration, and lens with cataracts (17-20). Intravitreal injection of Aβ causes RGC damage, illustrating Aβ toxicity to retinal tissue (21). Therefore, for diagnosis of AD, retinal scans have been used to identify Aβ plaque deposits.

Recently, FDA approved a carrot cell based system for production of the first human therapeutic protein (22). Oral delivery of chloroplast-derived therapeutics bioencapsulated in plant cells eliminates the need for expensive fermentation, purification, cold storage and transportation and sterile delivery (23). Bioencapsulation of therapeutic proteins by plant cell wall ensures their protection from proteolytic degradation in the stomach and facilitates their delivery to the circulatory system by the action of commensal microbes and receptors present in the gut (23). The delivery of fusion proteins across intestinal epithelium is facilitated by transmucosal carrier, CTB by binding to the ganglioside receptor (24).

SUMMARY OF THE INVENTION

In accordance with the present invention, a method for delivery of a therapeutic protein into the central nervous system (CNS) in a subject in need thereof is provided. An exemplary method comprises administering to the subject, a composition comprising a fusion protein comprising said therapeutic protein operably linked to cholera toxin B subunit (CTB polypeptide), wherein the fusion protein is effective to provide therapeutic benefit within the CNS of the subject. The fusion protein described above may be administered either systemically or orally. Many different proteins within the CNS (e.g., the brain, retina, spinal cord) may be targeted using the compositions and methods described herein. Such proteins include, without limitation, amyloid beta (Aβ), tau, α-synuclein, aspartyl protease β-site APP cleaving enzyme (BACE1), insulin receptor and transferrin receptor.

In a preferred embodiment of the method, the composition is administered orally and the fusion protein comprises CTB operably linked to myelin basic protein (MBP) forming CTB-MBP, said CTB-MBP being effective to i) reduce levels of amyloid beta protein in the brain; and/or ii) reduce amyloid levels in the retina; and/or iii) prevent loss of retinal ganglion cells; and/or iv) decrease the ratio of insoluble vs soluble amyloid beta protein42 in hippocampus; thereby providing therapeutic benefit to the subject, wherein said CTB-MBP fusion polypeptide is derived from a plastid transformed to express said CTB-MBP polypeptide.

In yet another aspect, the invention provides a composition derived from a plant effective for delivering the therapeutic protein across the blood-brain or retinal barrier, wherein the plant composition comprises a therapeutically effective amount of a CTB-therapeutic protein targeting fusion polypeptide. In certain aspects, the therapeutic protein targets a protein selected from the group consisting of Aβ, tau, α-synuclein, aspartyl protease β-site APP cleaving enzyme (BACE1), insulin receptor or transferrin receptor. In other embodiments, the composition comprises a fusion protein wherein CTB is operably linked to an antibody immunologically specific for the therapeutic protein. In a particularly preferred embodiment, the therapeutic fusion protein is CTB-MBP.

The plant of the invention comprises a plastid transformed with a stable plastid transformation and expression vector which comprises an expression cassette comprising, as operably linked components in the 5' to the 3' direction of translation, a promoter operative in said plastid, a selectable marker sequence, a heterologous polynucleotide sequence coding for said CTB-therapeutic protein polypeptide, transcription termination functional in said plastid, and flanking each side of the expression cassette, flanking DNA sequences which are homologous to a DNA sequence of the target plastid genome, whereby stable integration of the heterologous coding sequence into the plastid genome of the target plant is facilitated through homologous recombination of the flanking sequence with the homologous sequences in the target plastid genome. Also encompassed by the invention are plant progeny, plant parts, or seeds obtained from the plant described above.

In particularly preferred embodiments, the compositions are of pharmaceutical grade and are suitable for administration to human subjects.

DETAILED DESCRIPTION OF THE INVENTION

Figure 1:
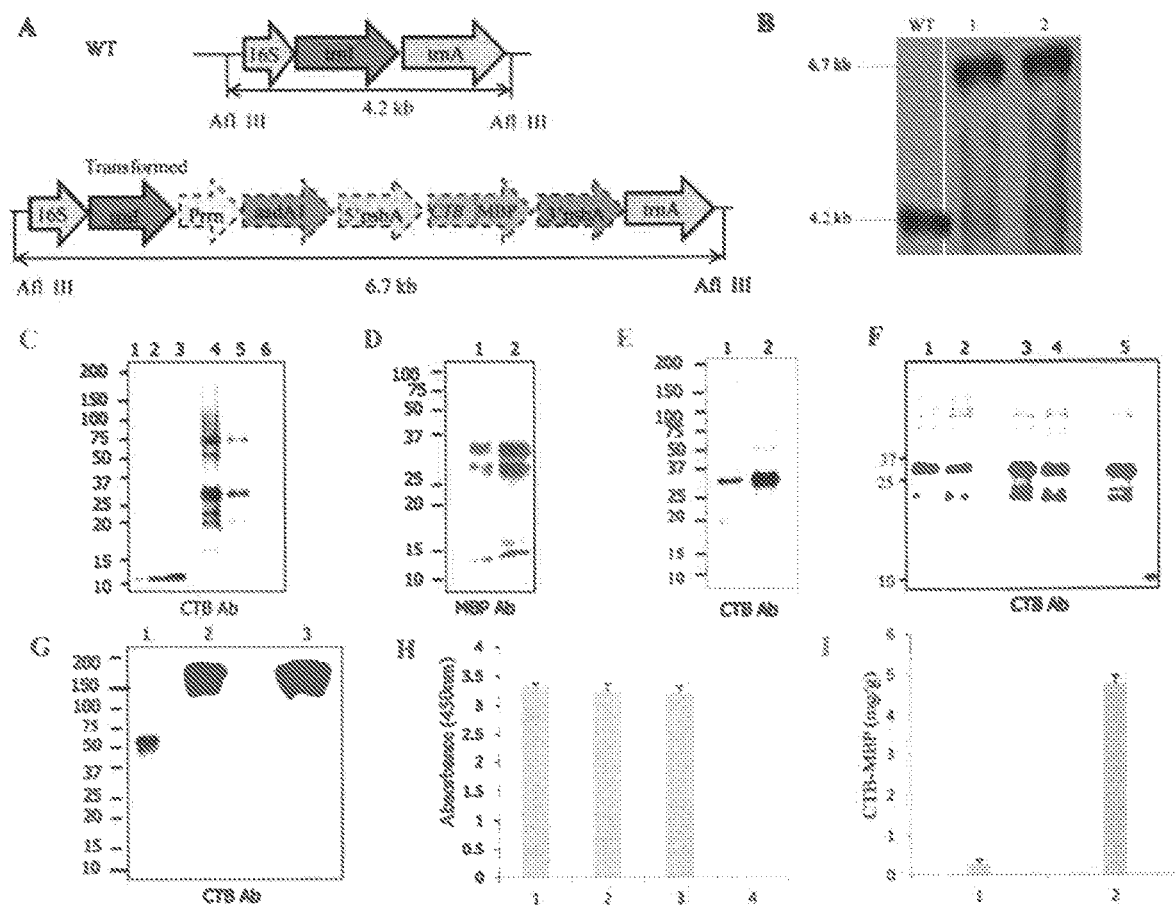
FIGS. 1A to 1I: Characterization of CTB-MBP transplastomic lines. (a) Schematic representation of Wild Type (WT) and transformed tobacco chloroplast genome. (b) Digestion with AflIII yields 4.2 kb and 6.7 kb fragments in WT and transplastomic lines (1, 2), respectively in Southern blot. Western blots of CTB-MBP expression in fresh (F) and lyophilized (L) transgenic plant extracts. (c) SDS-PAGE with anti-CTB antibody. Lane 1, 2, 3,—12.5 ng, 25 ng, 37.5 ng purified CTB standard; lanes 4, 5 & 6—20 µg of crude extract F, L and WT. (d) SDS-PAGE with anti-MBP antibody. Lane 2 & 3—20 µg of F and L respectively. (e) SDS PAGE with anti-CTB antibody for normalization of F and L transgenic plant proteins. In lanes 1 and 2, equal quantities (100 mg) of F and L samples were ground in 300 uL of extraction. (f) Western blot analysis showing long term stability of CTB-MBP (L) after storage at room temperature for seven months. Lane 1, 2, 3,4, 5 (November, January, March, April, May)—20 µg of L stored at room temperature for different durations, lane 6 —12.5 ng CTB standard. (g) Native PAGE probed with anti-CTB antibody. Lane 1—37.5 ng purified CTB standard; lane 2 & 3—2 µg of F and L respectively. (h) GM1 ELISA of purified CTB (25 ng), transgenic CTB-MBP protein in 20 µg of F, L and WT extracts in lane 1, 2, 3, 4 respectively. (i) Quantification of CTB-MBP protein (mg of protein/g of total leaf) in F and L plant extracts in lane 1 and 2 respectively.

Delivering neuro-therapeutics to target brain-associated diseases is a major challenge. Therefore, we investigated oral delivery of green fluorescence protein (GFP) or myelin basic protein (MBP) fused with the transmucosal carrier cholera toxin B subunit (CTB), expressed in chloroplasts (bioencapsulated within plant cells) to the brain and retinae of triple transgenic (3xTg) AD mice, across the blood-brain and retinal barriers. Human neuroblastoma cells internalized GFP when incubated with CTB-GFP but not GFP alone. Oral delivery of CTB-MBP in healthy and 3xTgAD mice shows increased MBP levels in different regions of the brain, crossing intact blood brain barrier. ThioflavinS stained amyloid plaque intensity was reduced up to 60% by CTB-MBP incubation with human AD and 3xTgAD mice brain sections ex vivo. Amyloid loads were reduced in vivo by 70% in hippocampus and cortex brain regions of 3xTgAD mice fed with bioencapsulated CTB-MBP, along with reduction in the ratio of insoluble Aβ42 to soluble fractions. CTB-MBP oral delivery reduced Aβ42 accumulation in retinae and prevented loss of retinal ganglion cells in 3xTgAD mice. Lyophilization of leaves increased CTB-MBP concentration by 17-fold and stabilized it during long-term storage in capsules, facilitating low-cost oral delivery of therapeutic proteins across the blood brain and retinal barriers.

While a myelin basic protein-CTB fusion protein is exemplified herein, other proteins could be delivered, or, in the alternative targeted with recombinantly produced therapeutic antibodies using the recombinant CTB fusion protein approach described. Such proteins include, without limitation, Aβ, tau, α-synuclein, aspartyl protease β-site APP cleaving enzyme (BACE1),insulin receptor and transferring receptor.

Definitions:

As used herein, the terms "administering" or "administration" of an agent, drug, or peptide to a subject includes any route of introducing or delivering to a subject a composition as described herein to perform its intended function. The administering or administration can be carried out by any suitable route, including orally, intranasally, parenterally (intravenously, intramuscularly, intraperitoneally, or subcutaneously), rectally, or topically. Administering or administration includes self-administration and the administration by another.

As used herein, the term "CTB" refers cholera toxin B subunit. Cholera toxin is a protein complex comprising one A subunit and five B subunits. The B subunit is nontoxic and important to the protein complex as it allows the protein to bind to cellular surfaces via the pentasaccharide chain of ganglioside.

As used herein, the term "chloroplast" includes organelles or plastids found in plant cells and other eukaryotic organisms that conduct photosynthesis. Chloroplasts capture light energy to conserve free energy in the form of ATP and reduce NADP to NADPH through a complex set of processes called photosynthesis. Chloroplasts contain chlorophyll. Chloroplasts have a higher copy number and expression levels of the transgene. Each chloroplast may contain up to 100 genomes, while each plant cell may contain up to 100 chloroplasts. Therefore, each plant cell may contain as many as 100000 chloroplast genomes which results in high expression levels of proteins expressed via the chloroplast genome. Chloroplasts further offer gene containment through maternal inheritance as the chloroplast genome is not transferred through pollen unlike nuclear genomic DNA. Chloroplasts have the ability to transcribe polycistronic RNA and can perform the correct processing of eukaryotic proteins including the ability to carry out post-translational modifications such as disulphide bonding, assembly of multimers and lipid modifications.

As used herein, a "composition," "pharmaceutical composition" or "therapeutic agent" all include a composition comprising a myelin basic protein comprising construct as described herein. Optionally, the "composition," "pharmaceutical composition" or "therapeutic agent" further comprises pharmaceutically acceptable diluents or carriers.

As used herein, the terms "disease," "disorder," or "complication" refers to any deviation from a normal state in a subject. In preferred embodiments, the methods and compositions of the present disclosure are useful in the diagnosis and treatment of neurological disorders such as Alzheimer's Disease (AD).

As used herein, by the term "effective amount," "amount effective," "therapeutically effective amount," or the like, it is meant an amount effective at dosages and for periods of time necessary to achieve the desired result.

As used herein, the term "expression" in the context of a gene or polynucleotide involves the transcription of prokaryotic genes at high level in plant chloroplasts.

As used herein, the term "preventing" means causing the clinical symptoms of the disease state not to develop, e.g., inhibiting the onset of disease, in a subject that may be exposed to or predisposed to the disease state, but does not yet experience or display symptoms of the disease state.

As used herein, the term "subject" refers to any animal (e.g., a mammal), including, but not limited to, humans, non-human primates, rodents, and the like, which is to be the recipient of a particular treatment.

As used herein, the terms "treating" or "treatment" or "preventing" refers to both therapeutic treatment and prophylactic or preventative measures, wherein the object is to prevent or slow down (lessen) the targeted pathologic condition or disorder.

As used herein, the terms "total leaf protein" (TLP) includes leaf amino acid compositions, enzymes, structural proteins and free protein amino acids.

As used herein, the term "vector" refers to a nucleic acid molecule capable of transporting another nucleic acid to which it has been linked.

The term "plant" as used herein includes, without limitation, tobacco, lettuce, tomato, carrot, barley, wheat, etc. Progeny, seeds, leaves, roots and other plant parts of the recombinant plants described herein are also within the scope of the invention.

The transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim, an in the latter instance, impurities ordinarily associated with the specified material(s). The term "consisting essentially of" limits the scope of a claim to the specified elements, steps or materials and those that do not materially affect the basic and novel characteristic(s) of the claimed subject matter.

Oral compositions produced by embodiments of the present invention can be administered by the consumption of the foodstuff that has been manufactured with the transgenic plant producing the plastid derived therapeutic protein. The edible part of the plant, or portion thereof, is used as a dietary component. The therapeutic compositions can be formulated in a classical manner using solid or liquid vehicles, diluents and additives appropriate to the desired mode of administration. Orally, the composition can be administered in the form of tablets, capsules, granules, powders and the like with at least one vehicle, e.g., starch, calcium carbonate, sucrose, lactose, gelatin, etc. The preparation may also be emulsified. The active immunogenic ingredient is often mixed with excipients which are pharmaceutically acceptable and compatible with the active ingredient. Suitable excipients are, e.g., water, saline, dextrose, glycerol, ethanol or the like and combination thereof In addition, if desired, the compositions may contain minor amounts of auxiliary substances such as wetting or emulsifying agents, pH buffering agents, or adjuvants. In a preferred embodiment the edible plant, juice, grain, leaves, tubers, stems, seeds, roots or other plant parts of the pharmaceutical producing transgenic plant is ingested by a human or an animal thus providing a very inexpensive means of treatment of or immunization against disease.

The following materials and methods are provided to facilitate the practice of the present invention.

Vector Construction, Regeneration and Confirmation of Transgene Integration:

Fusion construct was made with CTB and human MBP (hMBP) which were separated by glycine-proline-glycine-proline (GPGP) hinge to avoid steric hindrance. In addition, a furin cleavage site was introduced between the two proteins. The pLD-CTB-MBP vector was created and chloroplast transformation system was used to regenerate CTB-MBP transplastomic plant lines (30). Plant DNA isolation was followed by restriction digestion with AflIII and Southern blot to confirm integration of transgene and homoplasmy using hybridization with [$^{32}$P]α[dCTP]-labeled chloroplast flanking sequence probe containing trnI-trnA genes (30).

Expression and Preparation of Frozen and Lyophilized Plant Material:

Extracted proteins from plants at greenhouse were separated on SDS-PAGE gels as described before (43). The CTB-MBP fusion protein was also probed with rabbit anti-human MBP primary monoclonal antibody (1:1000, Abcam) followed by goat anti-rabbit IgG-HRP-conjugated secondary antibody (1:4000, Southern Biotech). CTB-MBP material was lyophilized and immunoblots and GM1 assays were performed as described before (43). Native PAGE was carried for detection of pentameric state of fusion protein as detailed elsewhere (47). For oral delivery, plant material was prepared by adding 4 mL and 1 mL of PBS to 500 mg of lyophilized CTB-MBP and 100 mg of fresh weight CTB-GFP, respectively and stored on ice right until oral gavage.

Mice and Oral Delivery Experiments:

For oral delivery of CTB-GFP, 6 weeks old healthy C57BL/6J mice (Jackson Lab) were used. Mice (n=5) were orally gavaged with bioencapsulated CTB-GFP (~200 mg/mouse/day) for three consecutive days. For oral delivery of CTB-MBP 13-15 months old (at the start of study, 7 male and 7 female) 3xTgAD mice (49), purchased from National Institute of Aging (NIA), were housed in University of Central Florida animal facility under controlled humidity, temperature e conditions. The lyophilized leaf material for oral gavage at dose 31.2 µg/300 ul/day of either plant bioencapsulated CTB-MBP (n=10) or WT (n=4) was delivered three times a week, for three months. A set of mice (n=4) were kept unfed.

Preparation of Tissues:

On the day of sacrifice, all mice were perfused with saline and brains were dissected. Right hemisphere of the brain from 3xTgAD mice was prepared for histological analysis in 4% paraformaldehyde and cryoprotected in 30% sucrose overnight whereas the three brain regions—cerebellum, hippocampus, and cortex were dissected from left hemisphere for Aβ measurements in biochemical analyses. For GFP measurements in healthy mice, blood samples were collected at 2 and 5 hours of last gavage at which mice were sacrificed, and tissue samples were collected for protein isolation. For oral delivery of CTB-MBP in C57 mice, tissues were harvested 5 hours after the last gavage and fixed overnight in 4% paraformaldehyde. Cryostat brain sections at the level of hippocampus were cut and mounted on Superfrost Plus slides. The sections were incubated in blocking solution (5% BSA+0.3% Triton X-100 in PBS) for 1 hour, followed by incubation with rabbit anti-MBP polyclonal antibody 1:100 (ab 65988, Abcam), which recognizes both human and endogenous mouse MBP, overnight at 4° C. The sections were then incubated with an anti-rabbit IgG secondary antibody conjugated to Alexa 594 (Molecular Probes/Invitrogen) for 1 hour at RT. Sections were washed in PBS containing the nuclear counterstain DAPI (4',6 diamidino-2-phenylindole), and mounted in Dako mounting media. (Scale bar=50 µm). For ex vivo studies, AD mice brain tissues were obtained from NIA and AD human brain tissues were obtained as described before (49).

ELISA and Immunoblotting From Mouse Brain Tissue:

Dissected hippocampal tissues from 3xTgAD mice were homogenized in RIPA buffer. The homogenate was ultra-centrifuged at 350,000 g for 20 minutes at 4° C. Supernatant was collected (soluble fraction) and pellet was dissolved in 2% SDS/PBS (insoluble fraction). Protein concentration was determined using Bicinchoninic Acid Protein Assay kit (Pierce, Rockford, Ill.). Protein samples (15 µg) were separated on 10-20% TrisTricine gels (BioRad cat. #456-3114, Hercules, Calif.) and transferred to 0.2 mm nitrocellulose membranes. Blots were probed with Beta Amyloid 1-42 (12F4) monoclonal antibody (biotin labeled) (COVANCE cat. # SIG-39144). Blots were reprobed with anti β-actin monoclonal antibody (Sigma-Aldrich; A2228) as a loading control. Visualization of specific bands was performed using Odyssey Infrared Fluorescence Imaging System (Odyssey; Li-Cor, Lincoln, Nebr.). For ELISA, both soluble and insoluble fractions were assayed for Aβ42 using commercial ELISA kit (Invitrogen Human Ab42 ELISA kit cat # KHB3441). GFP concentration in tissues was measured by GFP ELISA kit (AKR121, Cell Biolab Inc.). Results were compiled using SoftMax Pro software (Molecular Devices).

Immunohistochemistry and Thioflavin S Staining:

Brain cryosections (8 µm thick) from CTB-MBP orally delivered 3xTgAD mice were obtained using microtome slicing system (Microm HM 505N, Fischer). Adjacent sections were exposed for 60 mins to PBS containing 0.1% Triton X-100 (Sigma, St. Louis, Mo.) and 5% normal goat serum (NGS) (Invitrogen, Camarillo, Calif.) to block non-specific binding, followed by incubation with primary antibody, polyclonal anti-amyloid beta (1:200 Cell Signaling cat. #2454) overnight at 4° C. To test for nonspecific staining by secondary antibody, additional slides were processed in similar fashion with primary antibody excluded. All slides were then rinsed for 1 hr at room temperature in several changes of PBS and incubated in the dark for 1 hr at RT in PBS containing 5% NGS and fluorescent secondary antibody, Alexa Fluor 568-conjugated IgG (1:200). After counterstaining with Hoescht 33342 (Invitrogen), images were acquired by Nikon Eclipse TE2000-E fluorescence microscope and processed by NIS Elements for Advanced Research, with the input levels adjusted to span the range of acquired signal intensities. For each mouse, 5 adjacent sections were selected and from each section 3 random fields were analyzed. Total area of pixel intensity was measured with the automated measurement tools in NIS Elements software. The total intensity was averaged and expressed as normalized, corrected values. Statistical analysis for the data was analyzed by single factor ANOVA. Similarly, following PBS rehydration, adjacent five sections were stained with 0.02% ThS (Sigma) in 70% ethanol for 8 minutes. Slides were then rinsed in 50-80% ethanol and distilled water, respectively and cover slipped with DAPI solution for acquiring images.

For ex vivo brains from 24 months old 3xTgAD mice, 7 µm cryostat sections were mounted on slides. Seven adjacent sections were incubated with 25 µg or 50 µg/section of 33% purified CTB-MBP plant protein in PBS. Commercial CTB alone, BSA and WT plant protein were also used as controls. After 2 days of incubation at 37° C., sections were stained with ThS (27, 37), imaged and quantified as described above. For each of three ex vivo brains, 7 adjacent sections were selected and from each section 3 random fields were analyzed. Threshold intensity was based on the intensity of background staining in control sections. The selected threshold was held constant across all experimental sections. Ex vivo post mortem human brain tissues from Alzheimer's disease, were deparaffinized and rehydrated to ensure optimal staining. The slides were passed through xylene followed by graded washes of xylene and ethanol, with a final wash of pure water. Brain sections were incubated with 50 µg/section of 33% purified CTB-MBP or WT plant material. After 2 days of incubation at 37° C., sections were stained with ThS and DAPI to acquire images as described above. For each of the 5 AD human brain sections from different individuals, 2 random fields were analyzed and quantified Eye Tissue Processing, Immunofluorescence and Quantification:

For western blot analysis, fresh retina was dissected and processed the same way as described for brain tissues. For frozen sections, enucleated eyes were fixed in 4% paraformaldehyde at 4° C. overnight. Eyecups were cryo-protected in 30% sucrose/PBS for several hours or overnight prior to quick freezing in optical cutting temperature compound. Then 12 um thick sections were cut at 20-22° C.

A biotin labeled monoclonal antibody against Aβ-42 (1:100, COVANCE cat. # SIG-39144) was used. Sections were permeabilized with 1% Triton X-100 for 10 min, followed by blocking with 5% BSA. Sections were incubated in the primary antibody overnight at 4° C. and washed with PBS. Texas Red conjugated streptavidin was used (1:200, Vector Laboratories, Burlingame, Calif.) as secondary antibody. Slides were cover slipped using VECTASHIELD (Vector Laboratories, Burlingame, Calif.), and antibody labeling was examined with a Zeiss (AxioVision Carl Zeiss Micro Imaging, Thornwood, N.Y.) microscope equipped with epifluorescence illumination and a high resolution digital camera. For quantitative measurement of inner retinal neuron density, frozen sections were counterstained with H&E, the number of nuclei in the RGC layer was counted from at least 10 sections from each eye, 4 eyes from each group (untreated, CTB-MBP fed 3xTgAD, and age-matched healthy control mice). To detect apoptotic cells, an In Situ Cell Death Detection Kit based on TUNEL technology (Roche Applied Science) was used.

Cell Culture Studies with Bioencapsulated CTB-GFP:

M17 human neuroblastoma cells were cultured in Opti-MEM® I Reduced Serum Media supplemented with 10% FBS and 1% Penicillin/Streptomycin in a 37° C. humidified incubator with 5% $CO_2$. Treatment media consisted of only Opti-MEM® reduced serum media (2% serum) excluding both FBS and Penicillin/Streptomycin. Treatments were performed at ~70% confluency. Extracted CTB-GFP or control proteins (23.3nM) were incubated for 24 hours in triplicates. For negative controls, cells with no treatment, plant derived CTB-MBP, commercial GFP, WT plant material, and commercial CTB were used. After 24 hour incubation, cells were washed once with PBS. Live nonfixed cells were imaged using Nikon Eclipse, TE2000-E fluorescence microscope.

Statistical Analysis:

Single Factor ANOVA was used for statistical evaluation of data. Data are presented as the mean±SD. For biochemical and retinal data paired Student's t-test was used to assess significance between two groups. Differences were considered significant at $p<0.05$.

Study Approval:

All animal studies were performed under Institutional Animal Care and Use Committee-approved protocols. Postmortem brain tissues of AD subjects were obtained from John Hopkins University Alzheimer's Disease Center, Department of Pathology and their use was approved by appropriate Institutional Committees.

The following example is provided to illustrate certain embodiments of the invention. It is not intended to limit the invention in any way.

Example I

Here we report for the first time, oral delivery of bioencapsulated reporter and therapeutic proteins across blood and retinal barriers.

Myelin basic protein (MBP) a major structural protein of central nervous system (CNS) comprising ~30% of the total myelin protein, is essential for the formation of CNS myelin (25) contributing to the stability and maintenance of the sheath. In the early stages of AD, focal demyelination associated with Aβ plaques in white matter is observed in both human tissue and relevant murine models, but not in plaque free areas (26). Moreover, MBP has also been shown in vitro to possess intrinsic protease activity capable of degrading Aβ amyloid and the ability to bind Aβ amyloid and inhibit Aβ fibril formation (27, 28). Bioencapsulated MBP fused with CTB is hypothesized to cross BBB in vivo and degrade Aβ aggregates. Therefore, in this study we investigate oral delivery of bioencapsulated CTB-MBP in mouse or human brains with advanced AD for delivery across BBB and BRB.

Characterization of CTB-MBP Protein Expressed in Chloroplasts

The CTB-MBP construct is based on the pLD vector with trnI-trnA flanking sequences to facilitate homologous recombination (29) and the gene of interest is regulated by the psbA promoter and 5' untranslated region (UTR) to achieve high level expression. In the fusion construct, glycine-proline-glycine-proline hinge prevented steric hindrance between two proteins, psbA 3' UTR provided transcript stability, the aadA gene and ribosome binding site conferred spectinomycin resistance for selection (FIG. 1a). Transplastomic plants were produced through particle bombardment as described earlier (30). Transplastomic lines were confirmed by Southern blots conferring site specific integration of transgene into the spacer region between trnI and trnA genes. Digestion of untransformed (WT) plant DNA with AflIII showed 4.2 kb fragment after hybridizing with $^{32}$P-labeled trnI-trnA flanking probe and transplastomic CTB-MBP lines showed only the 6.7 kb fragment, confirming homoplasmy and site specific integration of transgene (FIG. 1b). Immunoblots probed with CTB (FIG. 1c) and MBP (FIG. 1d) antibody showed ~28.5 kDa fusion protein monomer, dimer at ~57 kDa and trimer ~86 kDa in CTB-MBP transplasomic lines. Fresh leaves expressed up to 2% of total leaf protein but a 17-fold enhanced antigen concentration was achieved by lyophilization of the plant material (FIG. 1 c, i). Equal loading of protein showed a significant difference in accumulation of CTB-MBP between fresh and lyophilized materials (FIG. 1e). Moreover immunoblots probed with CTB antibody showed that lyophilized material maintained stability at room temperature and protection from degradation over 7 months of storage (FIG. 1f).

The functionality of CTB-MBP fusion protein was evaluated by GM1 ELISA, where the ability of CTB to bind to GM1 receptors depends on its pentameric form. GM1 binding assay showed that pentamers of fresh weight and lyophilized CTB-MBP were formed, confirming proper folding and disulfide bond formation (FIG. 1h). Non-reducing native PAGE immunoblots probed with CTB antibody further confirmed formation of the pentameric structure (FIG. 1g), within transgenic chloroplasts, attesting functionality of CTB-MBP for in vivo studies. Lyophilization process preserved the folding and disulfide bonds of CTB-MBP protein even after prolonged storage at room temperature (FIG. 1f).

Oral Delivery of Bioencapsulated CTB-GFP and CTB-MBP Across BBB/BRB

Figure 2A:
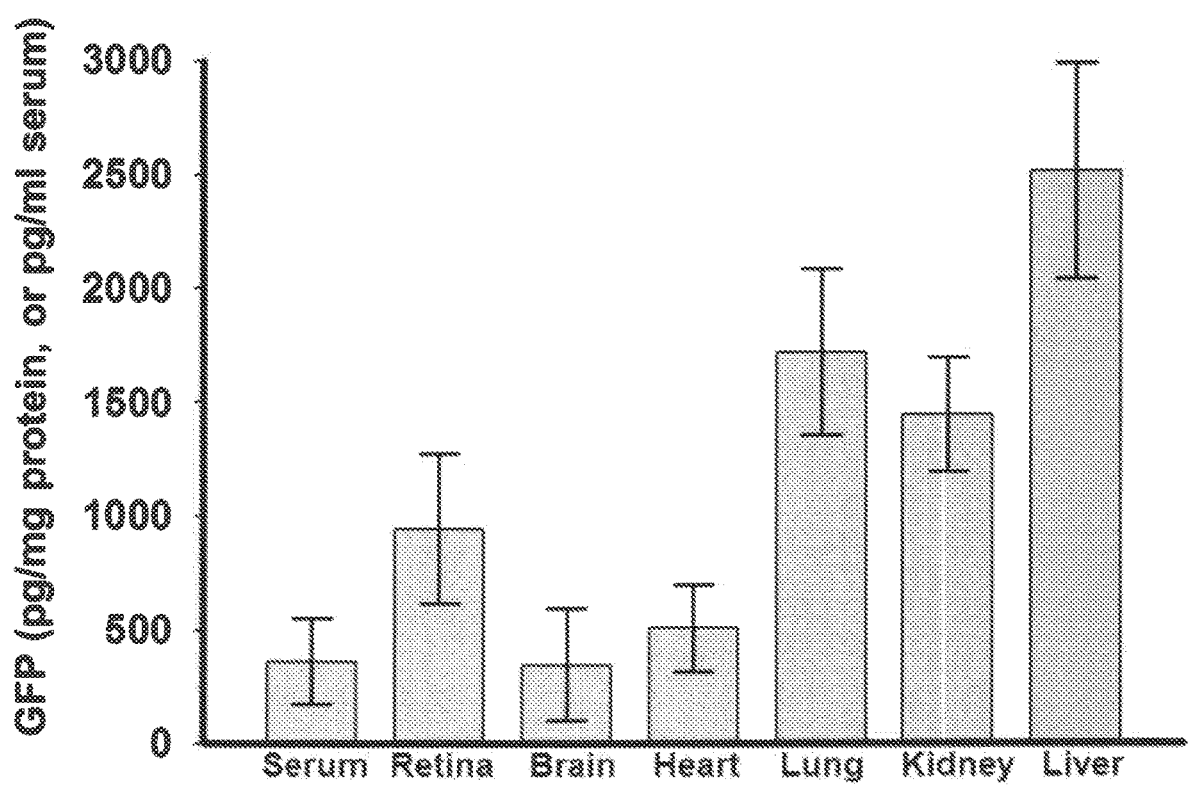
FIGS. 2A to 2F: Evaluation of GFP and MBP levels upon oral delivery of plant cells expressing CTB-fusion proteins. (a) GFP levels in different organs following oral gavage of CTB-GFP leaf material. Six weeks old mice were orally fed with CTB-GFP transgenic tobacco leaf suspension (~200 mg/mouse/day, n=5) for three consecutive days. Blood samples were collected at 2 hour and 5 hours after last gavage at which, mice were sacrificed and tissue samples were collected. GFP concentration in tissues was measured by ELISA. (b) Immunofluorescent detection of MBP in different regions of the C57B1/6J mouse brain fed with CTB-MPB or control untransformed (WT) leaf materials. Wild type C57 mice were orally gavaged with CTB-MBP or wild type leaf materials for 3 consecutive days. Tissues were harvested 5 hours after the last gavage and fixed overnight in 4% paraformaldehyde. Cryostat brain sections at the level of hippocampus were cut and mounted on Superfrost Plus slides. The sections were incubated in blocking solution (5% BSA+0.3% Triton X-100 in PBS) for 1 hour, followed by incubation with rabbit anti-MBP polyclonal antibody 1:100 (ab 65988, Abcam), which recognizes both human and endogenous mouse MBP, overnight at 4° C. The sections were then incubated with an anti-rabbit IgG secondary antibody conjugated to Alexa 594 (Molecular Probes/Invitrogen) for 1 hour at RT. Sections were washed in PBS containing the nuclear counterstain DAPI, and mounted in Dako mounting media (Scale bar =50 µm). I-VI: six layers of cortex. cc: corpus callosum. (c, d) Quantification of MBP levels in different regions of C57B1/6J mouse brain fed with CTB-MPB or control WT leaf materials. Immunofluorescence images were taken from fields within motor cortex (layer 1-3 and layers 4-6) and in CA1 and CA3 regions of Hippocampus with a 40× objective and constant exposure times on a Keyence confocal microscope. Threshold for images were set manually using NIH Image J software and fluorescence intensity was determined by using the measure module. Fluorescent intensity values in CTB-MBP fed mice were normalized to the control (WT leaf fed) levels. N=5. (e, f) Quantification of MBP levels in different regions of 3xTgAD mice brain fed with CTB-MPB or control WT leaf materials for three months. The values on y-axis of C and E represent the percentage of the control. N=8. P<0.01 (CTB-MBP vs WT) for all regions measured.
Figure 2B:
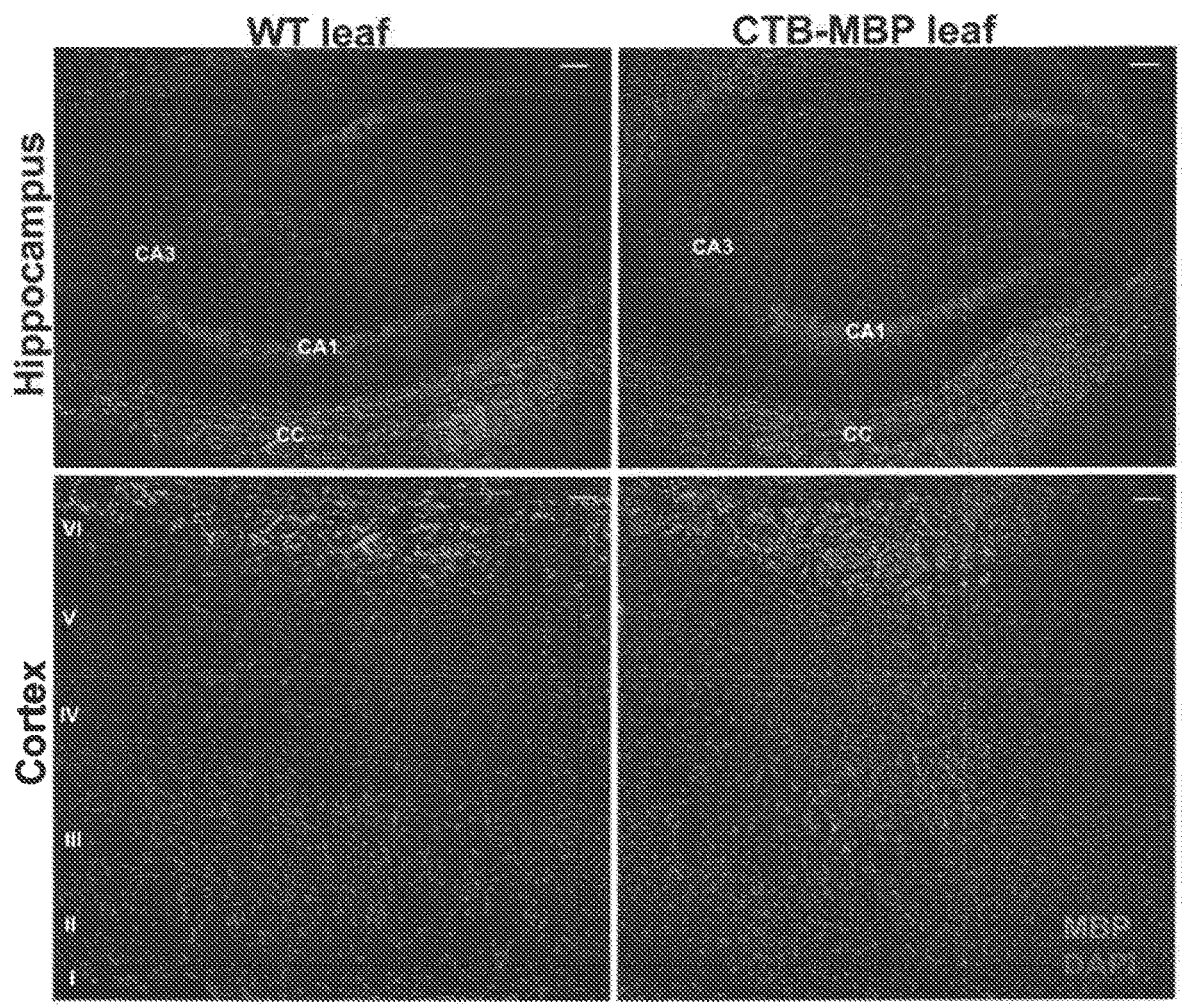
Figure 2C:
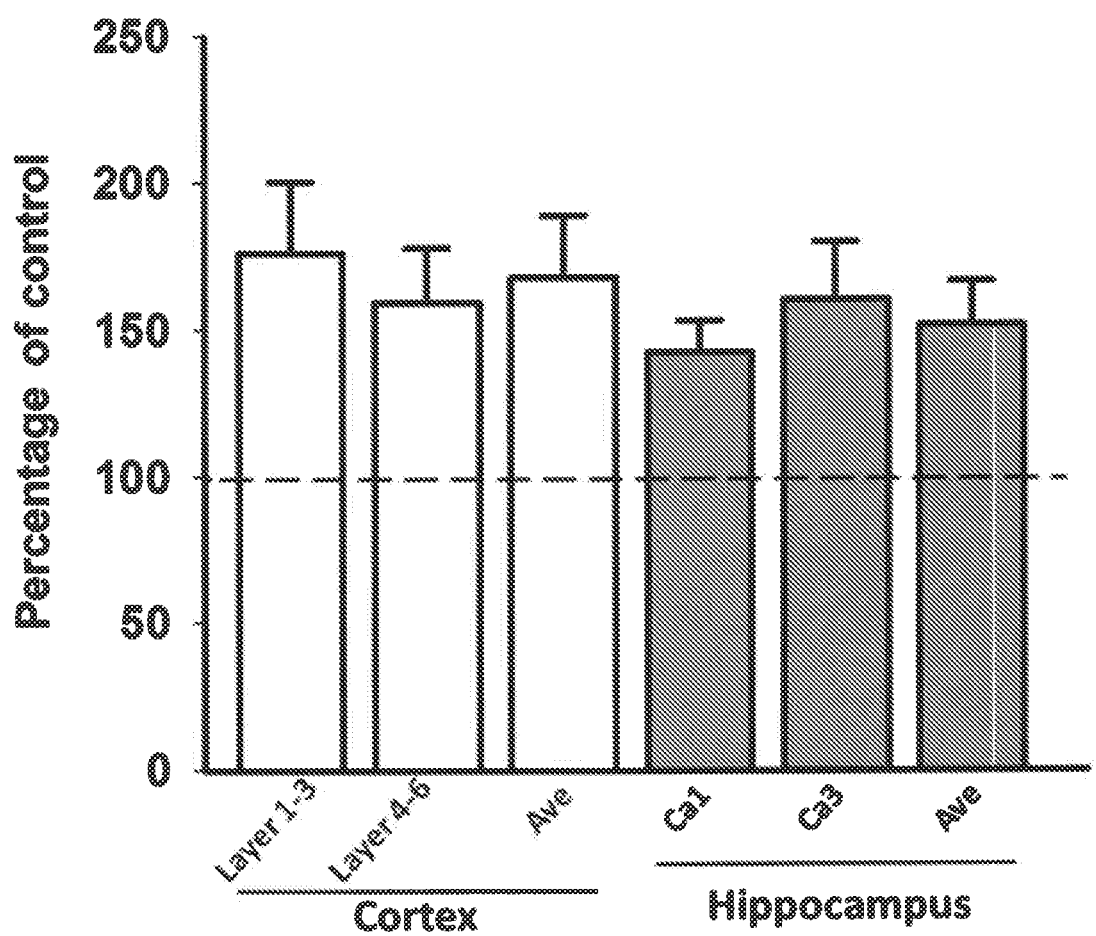
Figure 2D:
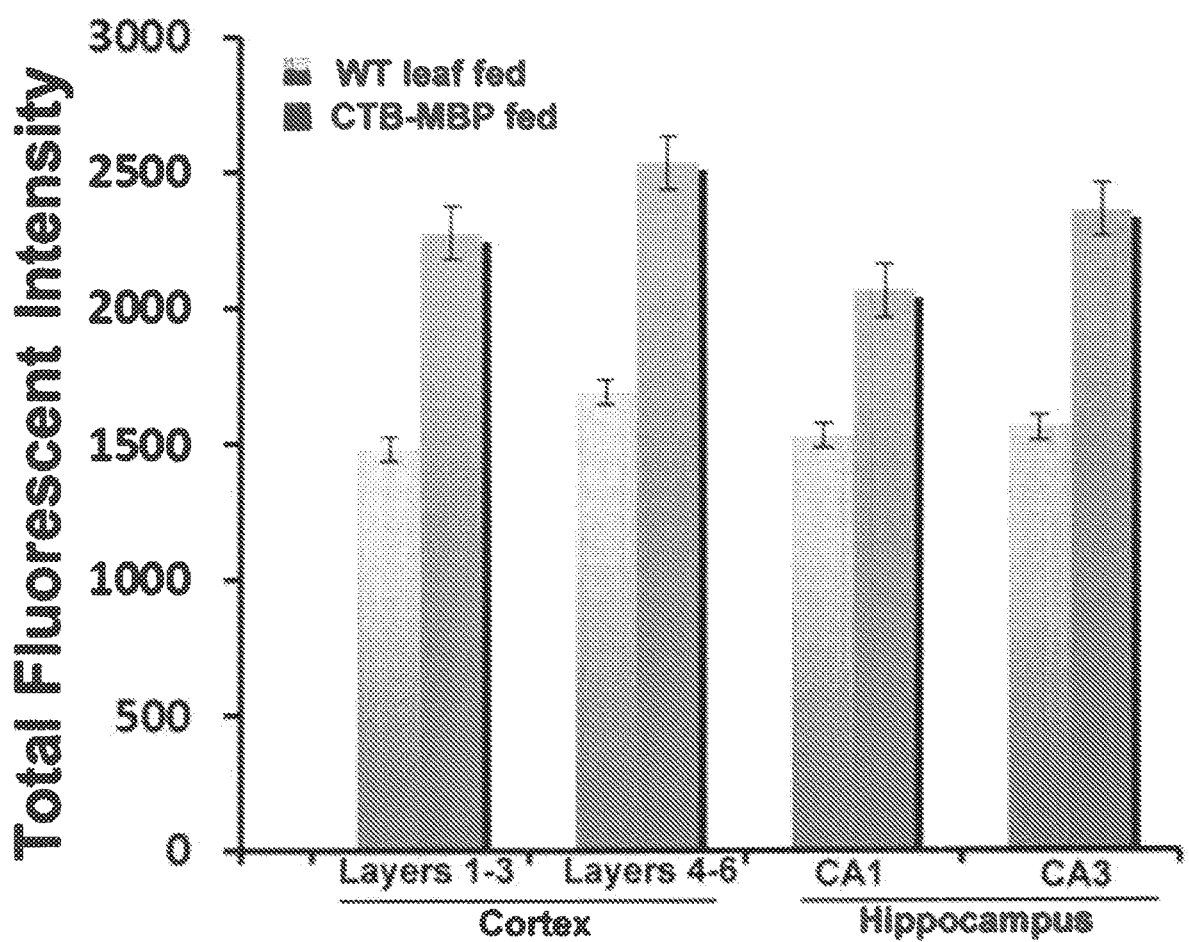
Figure 2E:
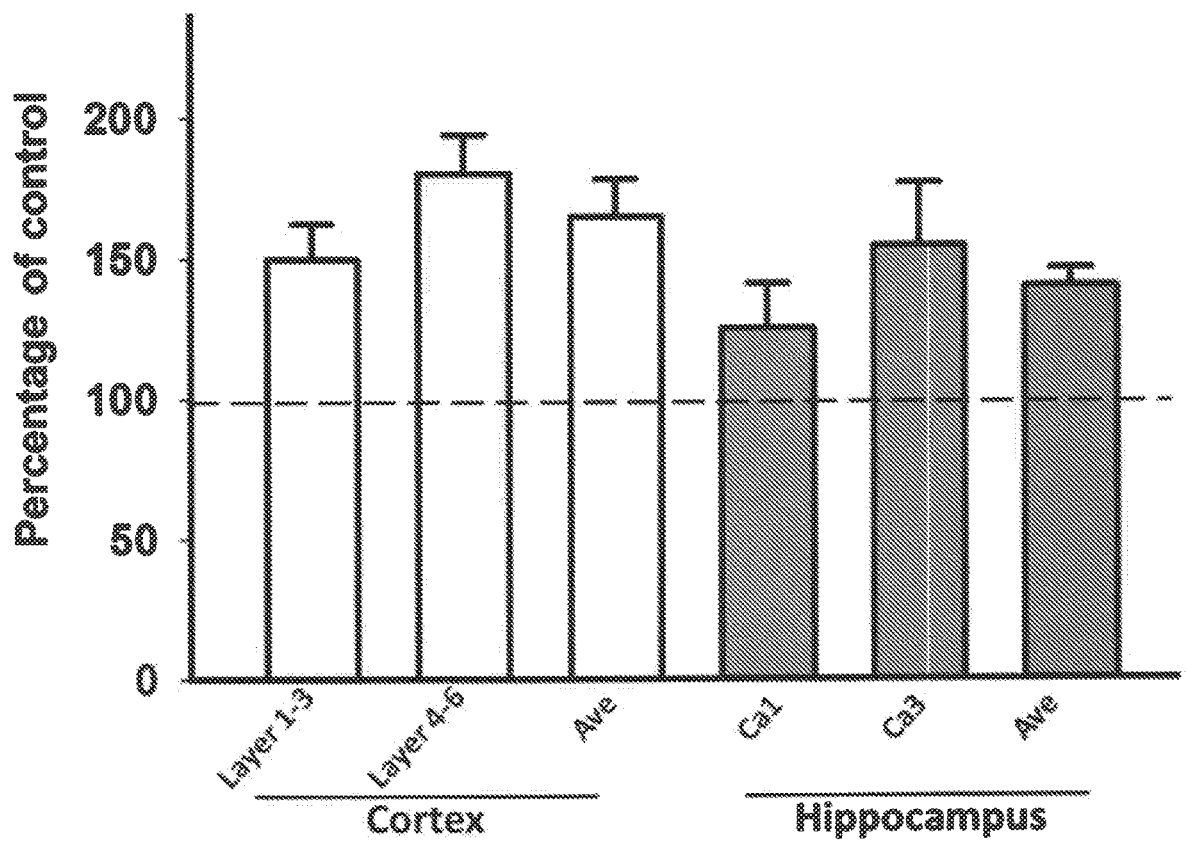
Figure 2F:
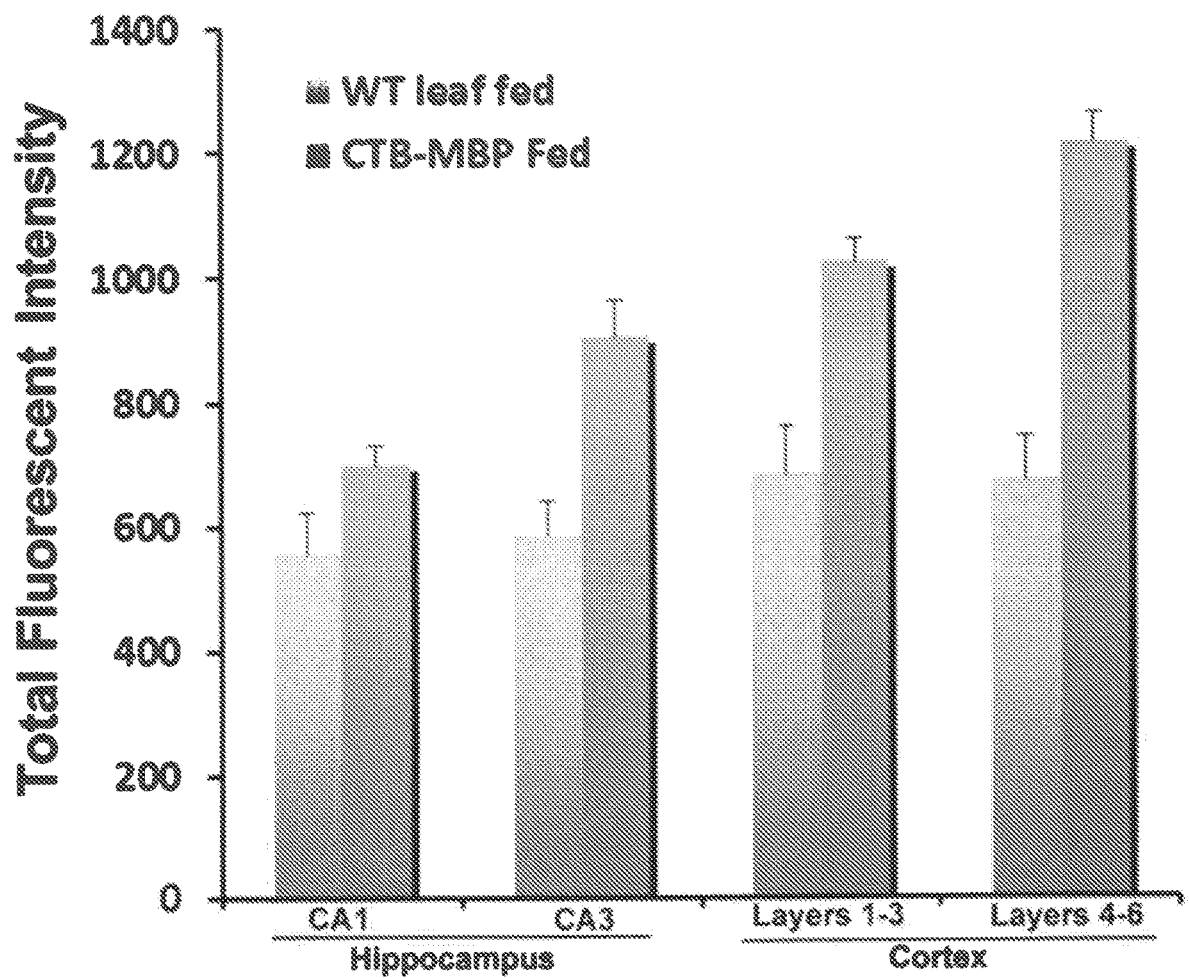

Oral gavage of CTB-GFP bioencapsulated plant cells created in a previous study (24) showed GFP fluorescence in mouse circulation system. Healthy C57BL/6J mice showed uptake of GFP in the sera and different organs (FIG. 2a) measured by using GFP ELISA kit. After 2 hours of gavage, 364 pg/ml of GFP was observed in the sera, and a lot more in other organs, showing very efficient and rapid delivery into the circulatory system. The highest GFP retention (2512 pg/mg) was observed in the liver, followed by lung (1720 pg/mg), kidney (1446 pg/mg) and heart (509 pg/mg). A concentration of 348 pg/mg and 945 pg/mg of GFP uptake in the brain and retinal tissue of mice, sacrificed after 5 hours of the last gavage, shows delivery of GFP across the BBB and BRB in healthy mice having fully intact BBB/BRB. Healthy mice orally gavaged with bioencapsulated CTB-MBP plant leaf material for three consecutive days showed MBP deposits in the hippocampus region when evaluated by immunofluorescence upon fixing brain tissue overnight (FIG. 2b). Wild type and 3xTg AD mice fed with CTB-MBP also showed increased MBP levels in different regions of the brain (FIG. 2c-f), confirming efficient transmucosal delivery of bioencapsulated proteins across BBB. Data for absolute values are provided along with percentage of respective control samples. The absolute fluorescence intensity values of MBP from wild type mouse brain are different from 3xTgAD mice because they are different mouse strains and different in their age. In addition, these experiments were done differently: 3 consecutive days of oral gavage of 6 weeks old C57BL/6J mice with CTB-MBP and sections were freshly cut and immune stained. On the other hand, 15 months old 3xTgAD mice were gavaged for three months and sections tissues were stored in the freezer for evaluation.

Role of CTB in Delivery of GFP into M17 Human Neuroblastoma Cells

Figure 3:
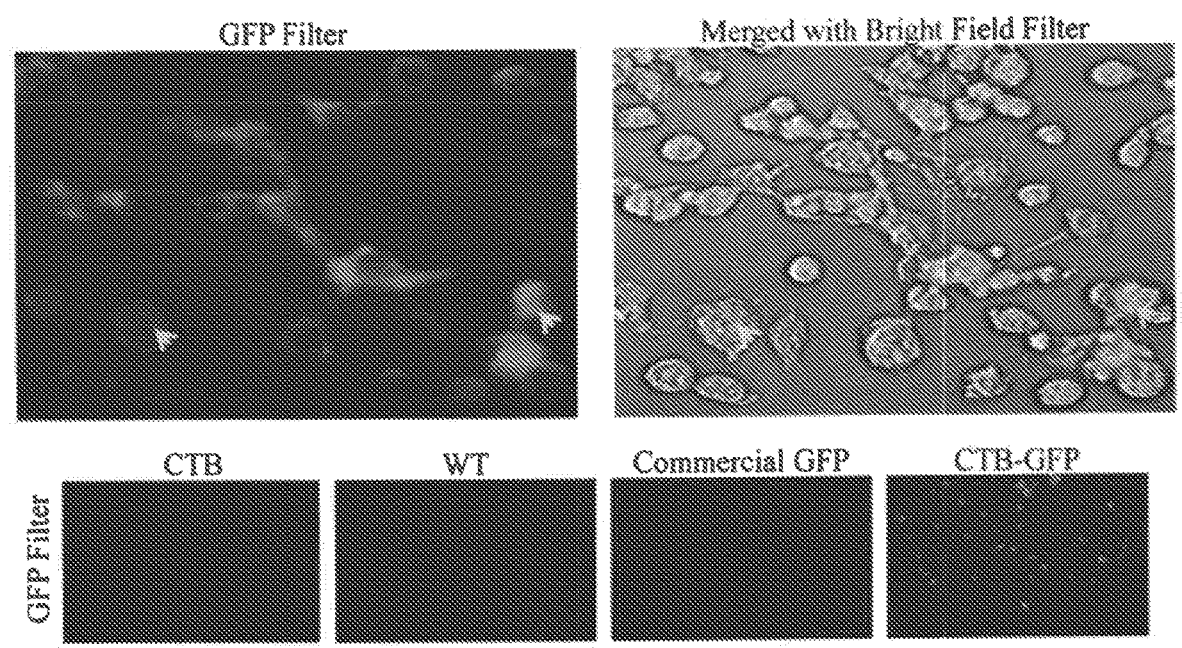
FIG. 3: Evaluation of GFP in M17 human neuroblastoma cells incubated with GFP or CTB-GFP by fluorescence microscopy. CTB-GFP was partially purified from transgenic leaf extracts. M17 cells were incubated with 23.3 nM of CTB alone or WT leaf extracts or purified GFP or CTB-GFP for 24 hours and processed for GFP fluorescence in parallel. Images of live non-fixed cells were taken at a magnification of 20× using GFP filter for 4s using Nikon Eclipse, TE2000-E fluorescence microscope. Representative images are shown in the bottom panel. Also shown are representative images of intracellular (arrowhead) GFP fluorescence in M17 cells treated with CTB-GFP.

M17 human neuroblastoma cells (31) incubated with GFP or CTB-GFP showed GFP fluorescence on the surface or within cells only with CTB-GFP and not with GFP alone (FIG. 3a). The absence of GFP within neuroblastoma cells shows the requirement for CTB as a carrier to deliver the fused protein across CNS cells. Inability of controls, particularly incubation with GFP without CTB fusion, to bind to M17 cells confirms that human neuroblastoma cells can uptake only the CTB-GFP fusion protein.

Ex Vivo Reduction of Amyloid Levels in 3xTgAD Mice Brains by CTB-MBP

Figures 4A, 4B:
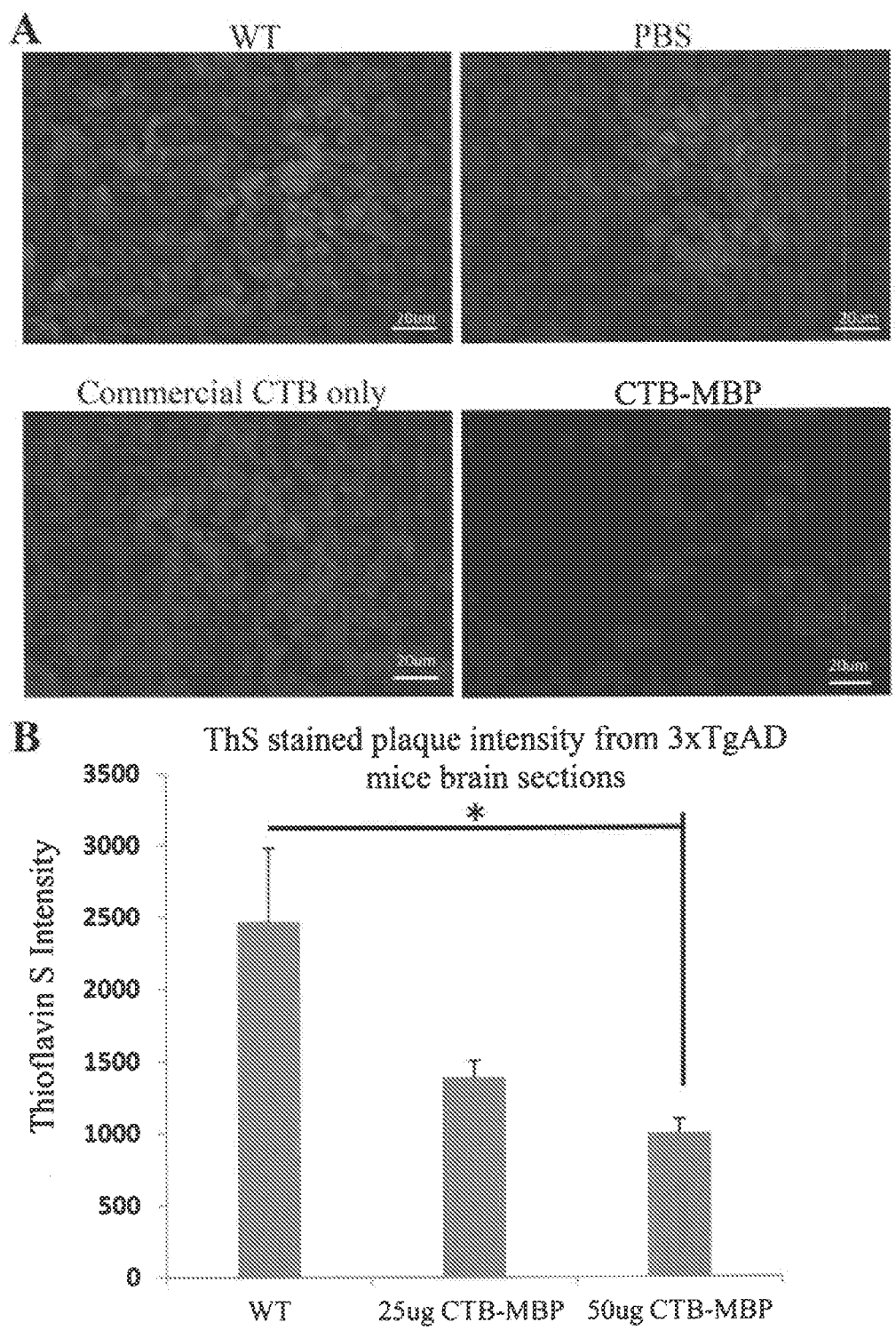
FIGS. 4A and 4B: Ex vivo evaluation of amyloid plaque load in 3xTgAD mouse brain tissue sections. (a) Sagittal serial sections of brains from 3xTgAD mice were incubated with 25 or 50 pg recombinant CTB-MBP protein purified from transgenic leaf extracts or 25 or 50 pg commercially available purified CTB for 2 days and then stained with 0.02% ThS solution to visualize the central dense core of compact amyloid (green)) by fluorescence microscopy. As controls, adjacent sections were incubated with 25 or 50 μg of WT leaf extracts or saline alone and processed for ThS staining in parallel. Shown are sections including the hippocampus and cortex of representative 24-month-old 3xTgAD mice (Scale bar: 20 um). (b) Quantification of the relative amounts of amyloid plaque load in the ThS stained sections after incubation with the indicated proteins or saline alone as described in (a). The mean plaque counts in the DG, CA1 and CA3 hippocampal and cortical regions per section (in cortex, mantle and pallium regions) were determined with NIS Elements for Advanced Research. The values in the histogram represent the mean ±S.D>n=63; *p<0.05 (Single factor ANOVA) relative to control.

Ex vivo studies of Thioflavin S (ThS) stained brain sections from 24 months old 3xTgAD mice showed reduction in amyloid plaques in hippocampus and cortex in a concentration-dependent manner when incubated with chloroplast-derived CTB-MBP (FIG. 4a). Reduction in ThS fluorescence up to 60% was detected after 2 days incubation with different concentrations of CTB-MBP plant derived protein, in adjacent brain sections (FIG. 4b). Incubations with protein extract from WT plants, phosphate buffered saline (PBS) or purified CTB under identical conditions did not show any effects in ThS intensity, suggesting that CTB-MBP, at an optimal concentration of 50 µg/section, is able to perform Aβ degrading enzymatic activity (27), thereby reducing their ThS fluorescence (FIG. 4b). Data shown is mean±S.D of values obtained from seven adjacent sections and evaluated from a total of 63 fluorescence images, confirming reproducibility of this observation.

Ex Vivo Reduction of Amyloid Levels in Post-Mortem Human AD Brains by CTB-MBP

Figures 5A, 5B:
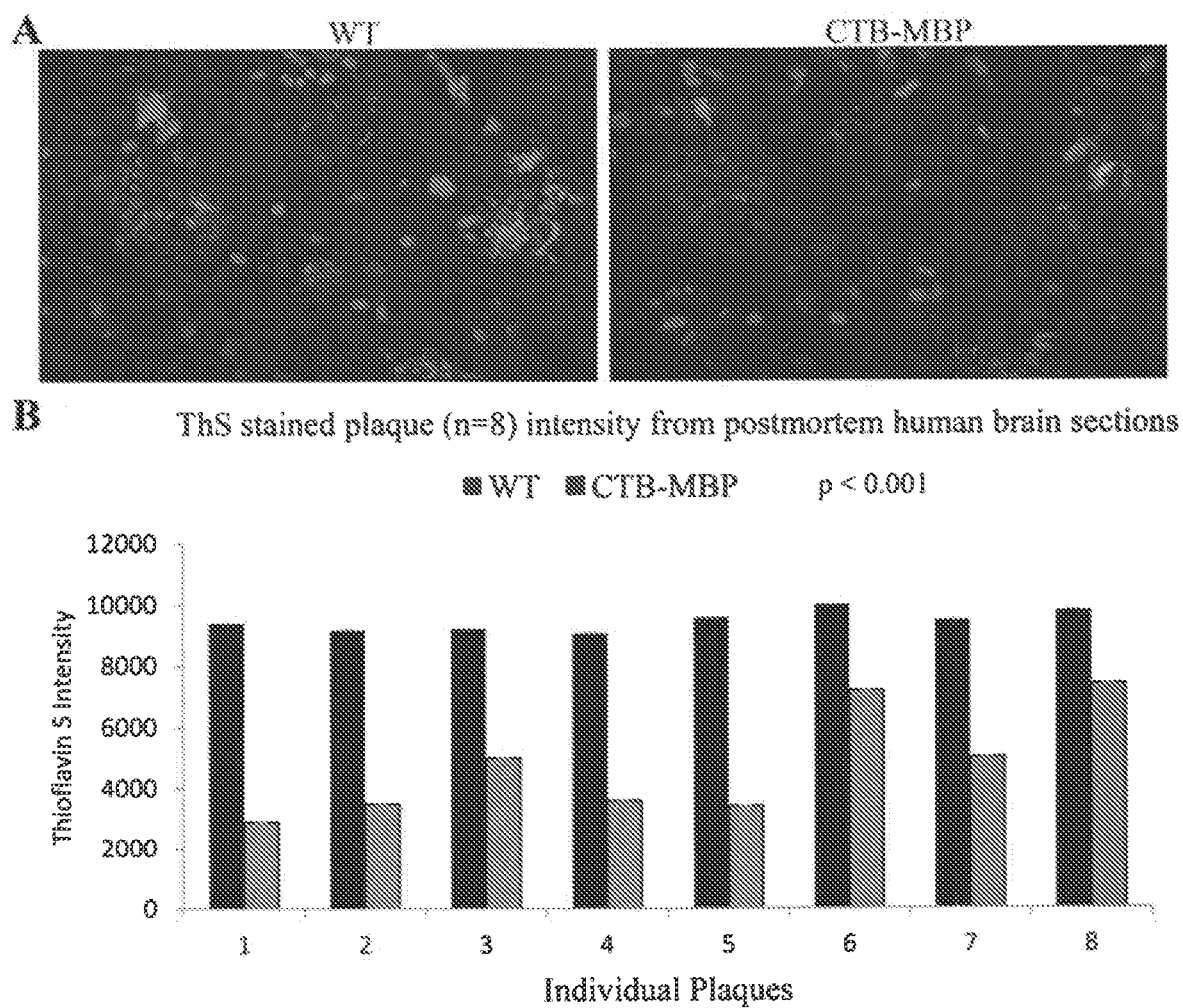
FIGS. 5A and 5B: Ex vivo evaluation of amyloid plaque load in post-mortem AD human brain tissue sections. (a) Sections of the parietal cortex from human AD were incubated with 50 μg recombinant CTB-MBP protein partially purified from transgenic leaf extracts or 50 μg of partially purified WT for 2 days and then stained with 0.02% ThS solution to visualize the central dense core of compact amyloid (green) and with DAPI to identify cell nuclei (blue) by fluorescence microscopy. (Scale bar: 20 um). (b) Quantification of the relative amounts of amyloid plaque load in the ThS stained sections after incubation with the indicated proteins as described in (A). The mean plaque counts per section were determined with NIS Elements for Advanced Research. The values in the histogram represent the mean ±S.D>n=8; *p<0.001 (Single factor ANOVA) relative to control.

Ex vivo studies of ThS stained brain sections of post mortem human brain tissues from advanced Alzheimer's disease patients were conducted with incubation of 50 µg/section CTB-MBP chloroplast expressed protein (FIG. 5a), a working concentration of MBP from ex vivo mice brain studies. Incubation with CTB-MBP showed up to 47% ThS fluorescence reduction of stained amyloid plaques in inferior parietal cortex of human brain sections (FIG. 5b) when compared to WT plant extract, indicating that MBP through its serine proteinase activity is able to degrade amyloid aggregates, thereby reducing their ThS fluorescence (FIG. 5b) in human brain tissues. Data shown is mean±S.D of values obtained from five sections of 5 different human AD postmortem brains and evaluated from a total of 10 fluorescence images. Although only limited human brain tissues were available for this study, we should point out reproducibility of these observations in brain tissues derived from 5 different individuals. It should be possible to achieve higher percentage of reduction in amyloid aggregates by further increasing concentration of CTB-MBP in ex vivo studies.

Figure 6:
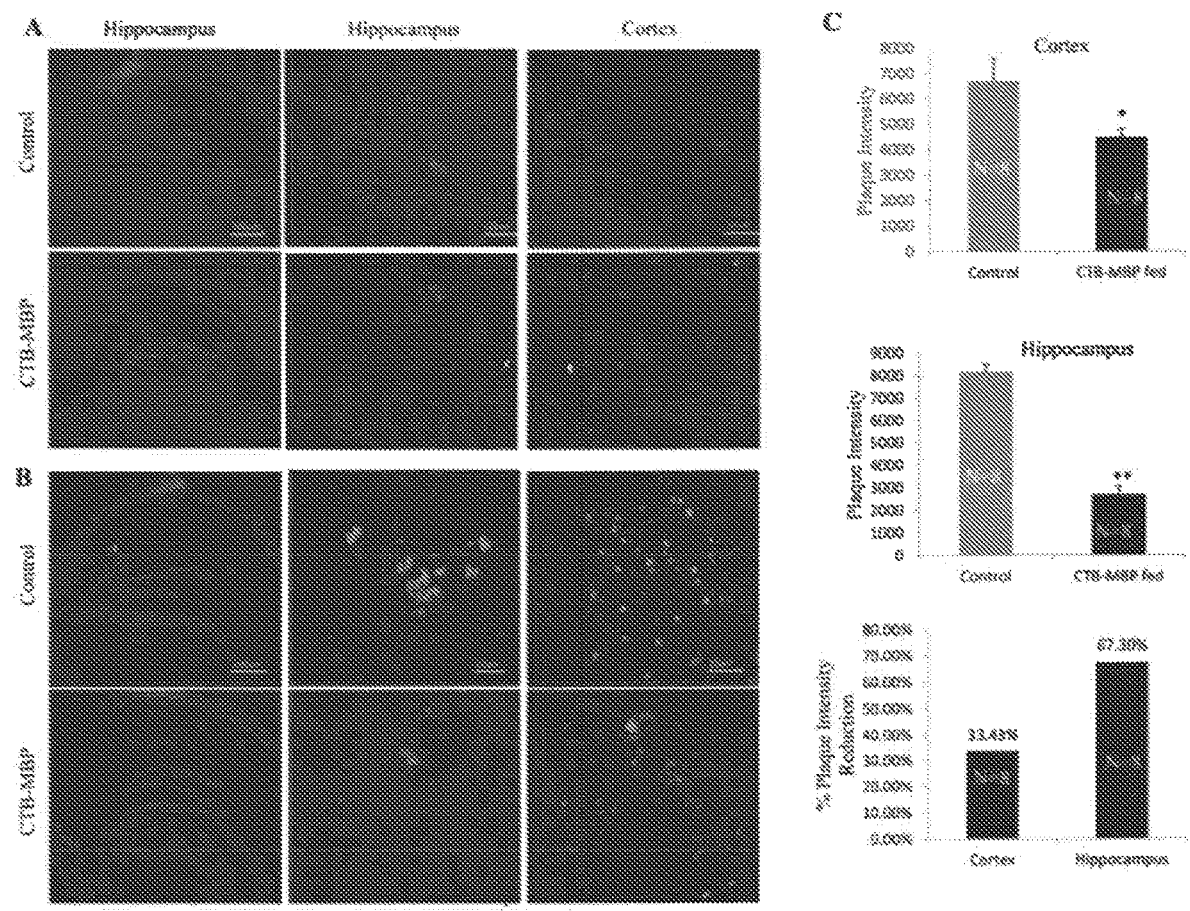
FIGS. 6A to 6C: In vivo evaluation of amyloid plaque load upon orally delivered CTB-MBP in 3xTgAD mice. (a, b) Representative images of the cortical and hippocampal brain sections of 12-14 months old 3xTgAD mice fed with either recombinant CTB-MBP bioencapsulated in plant cells (31.2 μg/300 ul/day; n=8 mice), WT leaf extracts (300 ul/day; n=4 mice), or unfed (n=4 mice). Sections were stained for amyloid plaques with either anti-Aβ antibody 2454 (red fluorescence; a) or ThS (green fluorescence; b) and with DAPI (blue) to label cell nuclei. Scale bar: hippocampus 100 um (i) and 10 um (ii) at different magnification, cortex 10 um (iii)). (c, d) Quantification of the relative amounts of amyloid plaque load in the anti-A(3 and ThS stained sections from the animals fed with CTB-MBP or WT protein extracts as described in (a, b). The mean plaque counts in the DG, CA1 and CA3 hippocampal and mantle and pallium cortical regions per section were determined with NIS Elements for Advanced Research. The values in the histogram represent the mean ±S.D>n=63; Single factor ANOVA *p<0.05 for cortex, **p<0.01 for hippocampus when compared to mice treated with WT leaf extracts and unfed.

In Vivo Reduction of Amyloid Levels in 3xTgAD Mice Brain After Oral Delivery of Bioencapsulated CTB-MBP The effect of oral delivery for a period of three months with either the bioencapsulated CTB-MBP, WT plant cells or unfed was evaluated in brain sections of 3xTgAD mice, which were 13-15 months old at the start of this study. Adjacent cortex and hippocampus sections of control and CTB-MBP treated mice stained with the anti-β-amyloid antibody (FIG. 6a, red) or ThS (FIG. 6b, green) were examined and quantified as described in methods. Most plaques were found in the hippocampus region, particularly DG, CA1 and CA3 sites, from where they started diffusing to the cortex as AD progressed. Aβ level reduction up to 67.3% and 33.4% in hippocampus and cortex respectively was observed (FIG. 6c) through immunostaining with anti-Aβ antibody upon oral delivery of CTB-MBP. Data shown is mean±S.D of values obtained from five adjacent sections from each mouse and evaluated from a total of 120 fluorescence images.

Evaluation of Amyloid Levels In Vivo in 3xTgAD Mice Brain

ThS stained plaque number and fluorescence intensity was also reduced up to 70% and 40%, respectively (FIG. 7a); quite consistent across 8 groups of age matched 3xTgAD mice upon oral delivery of CTB-MBP leaf material. Data was obtained as described before. Aβ peptide is produced in the brain where it normally remains in a soluble state and its function is still largely unknown. Accumulation, aggregation and deposition of Aβ peptides are pathological hallmarks in the AD brains and are found in the insoluble state (32).

Figure 7:
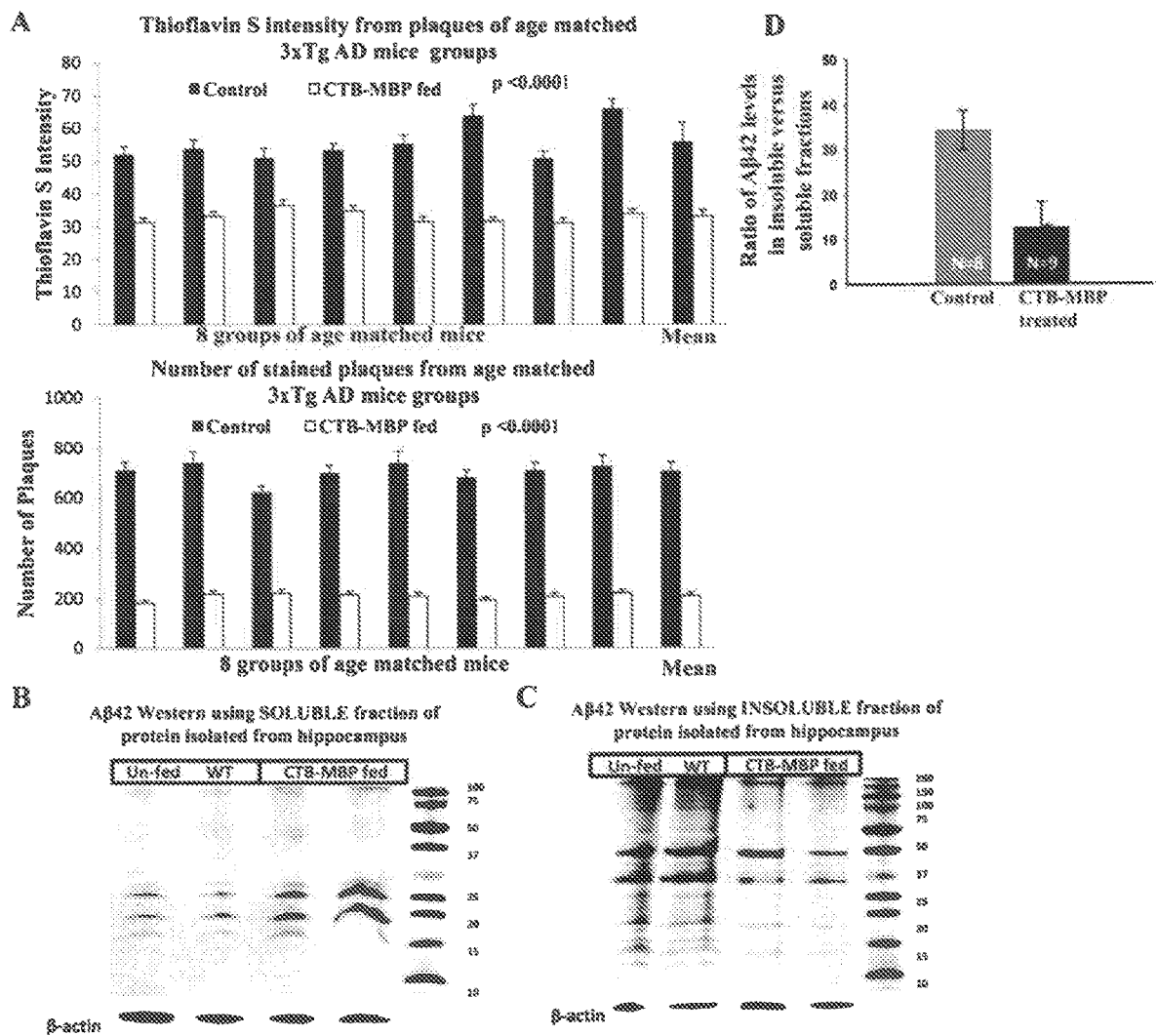
FIGS. 7A to 7D: Quantitative evaluation of amyloid levels in 3xTgAD mice upon CTB-MBP oral delivery. (a) Eight groups of age matched 3xTgAD mice fed with CTB-MBP showed consistent reduction in ThS intensity stained amyloid plaques. Evaluation of (b-d) Total Abeta(40/42) levels were measured by immunoblotting using anti-Aβ42 antibody, 12F4 (b,c) and ELISA (d),*p<0.05.

Therefore, we investigated the effect of MBP on Aβ-42 levels from soluble and insoluble fractions of protein extracts isolated from hippocampus of CTB-MBP fed and control 3xTgAD mice by both ELISA and western blotting using anti-Aβ42 specific antibody. The high molecular weight Aβ-42 aggregates were reduced in the insoluble fractions of hippocampus with corresponding increase of Aβ-42 in the soluble fraction in mice fed with bioencapsulated CTB-MBP, when compared with unfed or WT fed mice (FIG. 7 b, c). The ratio of Aβ42 levels in the insoluble versus soluble fractions of proteins isolated from hippocampus, measured by ELISA, showed a 2.7 fold decrease (FIG. 7d) in CTB-MBP fed mice when compared to respective controls.

Figure 8:
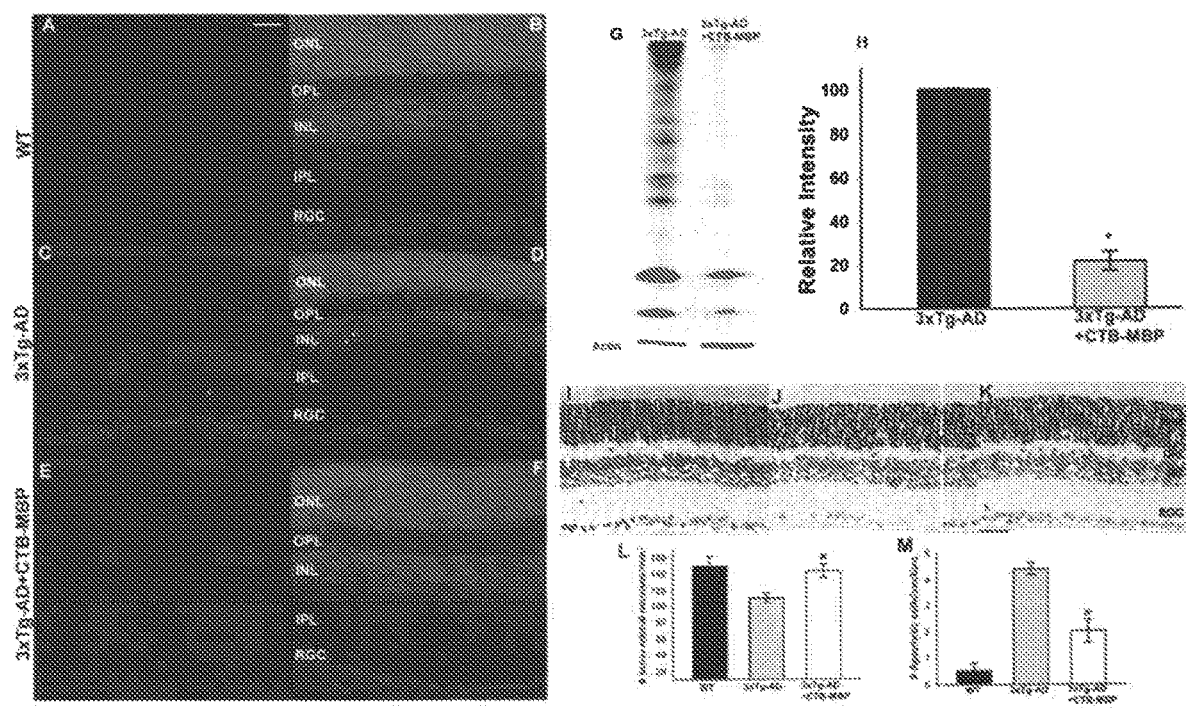
FIG. 8A to 8M: Evaluation of Aβ1-42 and inner retinal cells in 3xTgAD mice upon oral delivery of CTB-MBP. (a, c, e) The Aβ1-42 was detected by immunofluorescence using a biotin conjugated monoclonal antibody to Aβ1-42 followed by Texas Red-Streptavidin counter-stained with DAPI (b, d, f) (g) Western blot of retinal proteins isolated from untreated and CTB-MBP fed 3xTgAD mice using antibody against Aβ1-42. (h) Quantitative analysis of western blot data (n=4). The protein levels were normalized to those of actin and the densitometric value from each of the treated eyes is expressed as a percentage relative to the untreated eyes, *p<0.01. (i-k) Representative micrographs of retinal cross-sections from age-matched healthy control (i), untreated 3xTgAD (j), and CTB-MBP fed 3xTgAD mice (k). (l) Quantitative measurement of cell density in the RGC layer. (m) Quantitative measurement of apoptotic cells detected by TUNEL assay. *p<0.01 (vs untreated 3xTgAD eyes; n=4). Scale=20 μm. ONL: outer nuclear layer; OPL: outer plexiform layer; INL: inner nuclear layer; IPL: inner plexiform layer; RGC: retinal ganglion cell layer.

Reduction of Amyloid Level and Protection of Retinal Ganglion Cells in Mouse Retina After Oral Delivery of Bioencapsulated CTB-MBP In addition to cognitive and behavioral deficits, visual abnormalities are also frequently seen in AD patients. Therefore, we examined the 3xTgAD mouse eyes from animals that received oral gavage of bioencapsulated CTB-MBP plant leaf material for three months as well as eyes from age-matched untreated 3xTgAD and healthy mice. Amyloid deposit in the retina was evaluated by immunofluorescence using a biotin labeled monoclonal antibody specific for Aβ1-42. Intense staining for Aβ1-42 was detected in the inner retina, primarily in the RGC layer in 3xTgAD mice, but almost undetectable in healthy and 3xTgAD mice fed with CTB-MBP leaf materials (FIG. 8a-f). The retinal level of Aβ1-42 was also evaluated by western blotting using the same antibody and there was more than 60% reduction in the retinae from CTB-MBP fed mice, especially among high molecular weight peptide aggregates (FIG. 8 g, h). The retinae of 3xTgAD mice also showed marked loss of RGCs and increase of apoptotic cells detected by TUNEL assay compared to age-matched control mice (FIG. 8, I-M). Amyloid deposit and apoptotic cells are significantly reduced in mice fed with CTB-MBP and loss of RGCs was restored.

Discussion

Results of investigations show efficient in vivo oral delivery of chloroplast expressed CTB-fusion proteins across BBB and BRB. The native confirmation of CTB pentamers facilitates binding to the intestinal GM1 receptors and releases the fused protein to the circulatory system when orally administered. The mechanism of CTB binding to GM1 is well known (33). A recent study has shown that polymeric nanoparticles coated with GM1 binding peptide promoted transcytosis across the BBB (34). Presence of a voltage independent GM1 associated with a $Ca^{2+}$ channel has also been observed using CTB induced $Ca^{2+}$ influx in neuroblastoma cells (31). Direct evidence for crossing of BBB or BRB by CTB fusion proteins has been provided in our study by: 1) entry of CTB-GFP but not GFP into neuroblastoma cells; 2) presence of GFP in brain tissues upon oral delivery of CTB-GFP; 3) increase in MBP in brain tissues upon oral delivery of CTB-MBP; 4) decrease in amyloid plaques in 3xTgAD mouse brain slices in ex vivo studies with CTB-MBP incubation with thioflavin S staining; 5) decrease in individual amyloid plaques in human Alzheimer's brain slices in ex vivo studies with CTB-MBP incubation with thioflavin S staining; 6) decrease in amyloid plaques in 3xTgAd mouse brain upon oral delivery of CTB-MBP bioencapsulated in plant cells (thioflavin S staining and immunofluorescence images and quantitation); 7) removal of amyloid beta plaques in 3xTgAd mouse retina upon oral delivery of CTB-MBP. All these independent lines of investigations provide direct evidence for CTB fusion proteins crossing BBB and BRB, the key finding of this research project.

When compared with significant GFP delivery observed in the brains of healthy mice with intact BBB, the amount of CTB fused protein delivered across impaired BBB in AD brains is anticipated to increase further. BBB impairment is associated with more rapid progression in AD (35). Previous literature (27, 28) has shown that MBP inhibited Aβ fibril formation, where binding site for Aβ is situated at N terminal 64 amino acids of MBP. Inhibition of fibril assembly by N terminal domain of MBP was observed. MBP may directly degrade amyloid beta peptide aggregates/plaque (36) due to its intrinsic proteinase activity as also shown in our ex vivo studies. MBP may prevent Aβ peptide aggregation and plaque formation by direct binding of MBP through its N-terminal domain (27). It is likely that both mechanisms may take place, since a substantial fraction of the fusion protein will likely be cleaved in the circulation, as well as at target cells upon uptake. Our data shows increased MBP levels in different regions of the brain from animals fed with CTB-MBP. Our results clearly demonstrate the uptake of CTB-MBP into different regions of the brain via oral delivery of the protein bioencapsulated in plant cells.

It is well known that Thioflavin S staining is specific for AB-immunoreactive deposits in the brain and computer algorithm to detect such neurons have been developed (37). This study also shows significant reduction of ThS stained amyloid deposits in advanced human AD post mortem brain sections, when incubated with CTB-MBP. However in each brain section, obtained from different individuals suffering with Alzheimer's disease at an advanced stage, consistent reduction of ThS staining was observed upon incubation with chloroplast-derived CTB-MBP. Similarly, we observed significant concentration-dependent degradation and/or reduction of amyloid levels in the brains of old 3xTgAD mice upon CTB-MBP incubation.

We observed that 3xTgAD mice brain showed a significant decrease of amyloid levels when fed with CTB-MBP, particularly in dentate gyrus, CA1 and CA3 regions of hippocampal and in cortical brain regions, which are known to carry the most amyloid burden in transgenic AD mice as well as in human AD (38). Moreover, ThS positive amyloid deposits were observed in the areas of anti-amyloid immunoreactivity by staining hippocampus in adjacent brain sections in in vivo studies with anti-amyloid antibody and ThS. Moreover, reduction in Aβ plaque number and ThS intensity was uniform in CTB-MBP fed mice. Histological analyses confirm quantitative as well as qualitative reduction of Aβ accumulation through MBP in 3xTgAD mice and human AD.

Furthermore, biochemical analyses and quantitation of Aβ42 levels show a 2.7 fold decrease in the ratio of insoluble versus soluble Aβ42 protein levels in the hippocampus of 3xTgAD mice, demonstrating reduced insoluble aggregates in CTB-MBP fed mice when compared to control analyzed by both immunoblotting and ELISA. In healthy brains, at normal physiological states, Aβ exists as a low molecular weight protein in the soluble form that regulates synaptic functions in the neuronal metabolism (39). Therefore, soluble Aβ is essential for synaptic plasticity and neuronal survival. The clearance of amyloid load in this study warrants behavioral studies. However this should be done in younger mice at the early onset of AD rather than in highly advanced stages of AD used in this study. Although a number of studies correlate accumulation of Aβ plaques to dementia, a few recent studies have questioned such direct correlation because one third of people with plaque in their brains never show cognitive decline. However, a recent study (40) has resolved this controversy by demonstrating that memory decline is associated with spatial patterns of amyloid deposition rather than total amyloid burden.

Moreover, we also found increased accumulation of Aβ42 levels, loss of retinal ganglion cells and increased number of apoptotic cells in the retina of 3xTgAD mice when compared to age-matched healthy control mice. These retinal pathologies are significantly reduced in mice fed with chloroplast-derived CTB-MBP, suggesting that orally administrated CTB-MBP can be delivered to retina crossing BRB, presumably by a similar mechanism mediated by GM1 receptors discussed above. These results demonstrate that this strategy could be used to deliver other therapeutic proteins for retinal diseases. It is surprising that CTB-MBP treatment prevented the loss of RGCs. Since the treatments started in older mice (13-15 month old) for three months and RGCs do not regenerate, it is possible that the loss of RGCs is more prominent in older mice. Alternatively, although not mutually exclusive, the density of RGCs was counted from H&E stained sections, which may have included other cell types in this layer, such as astrocytes, pericytes and endothelial cells, CTB-MBP treatment may also prevent the loss of these cell types, or may promote their proliferation.

Active and passive immunotherapies have been reported to target Aβ in clinical studies (41) through immunization, but recent disappointment with bapineuzumab, a humanized anti-amyloid antibody in clinical trial III calls for alternative strategy for Alzheimer's drugs and therapies. Restricted delivery of monoclonal antibody to the brain, significantly contributed to the failure of this study and other studies.

Along with an efficient oral delivery of antigen through plant bioencapsulation, chloroplast transformation method offers an inexpensive production, storage and transportation of biopharmaceutically important proteins (23, 42). Lyophilization of plant cells increased CTB-MBP concentration, facilitating storage of capsules at room temperature for several months without any degradation of therapeutic protein (43, 44). CTB is an FDA approved antigen (45) and MBP is naturally in circulation in the human sera. Side effects of CTB have been already investigated for higher doses than used in this study. CTB fused autoantigens are not immunogenic but suppress formation of antibodies (46-48). Plant cells are routinely consumed and so bioencapsulation of CTB-MBP per se within plant cells shouldn't cause toxicity concerns. Recently, FDA approved a carrot cell based system for production of the first human therapeutic protein (22). Therefore, receptor mediated oral delivery of therapeutic proteins to the circulatory system and across BBB and BRB, barriers that protect the brain and retina, provides for further advances in human clinical studies.

REFERENCES

1. Luissint, A C, Artus, C, Glacial, F, Ganeshamoorthy, K and Couraud, P O (2012). Tight junctions at the blood brain barrier: physiological architecture and disease-associated dysregulation. Fluids Barriers CNS 9: 23.
2. Pardridge, W M (2012). Drug transport across the blood-brain barrier. J Cereb Blood Flow Metab 32: 1959-1972.
3. Lippmann E S, Azarin, S M, Kay, J E, Nessler, R A, Wilson, H K, Al-Ahmad, A et al. (2012). Derivation of blood-brain barrier endothelial cells from human pluripotent stem cells. Nat Biotech 30: 783-791.
4. Gabathuler, R (2010). Approaches to transport therapeutic drugs across the blood-brain barrier to treat brain diseases. Neurobiol Dis 37: 48-57.
5. Thrimawithana, T R, Young, S, Bunt, C R, Green, C and Alany, R G (2011). Drug delivery to the posterior segment of the eye. Drug Discov Today 16: 270-277.
6. Rizzolo, L J, Peng, S, Luo, Y and Xiao, W (2011). Integration of tight junctions and claudins with the barrier functions of the retinal pigment epithelium. Prog Retin Eye Res 30: 296-323.
7. Bucolo, C, Drago, F and Salomone, S (2012). Ocular drug delivery: A clue from nanotechnology. Front Pharmacol 3: 188.
8. Alzheimer's Association, Thies, W and Bleiler, L (2011). 2011 Alzheimer's disease facts and figures. Alzheimers Dement 7: 208-244.
9. Wimo, A and Prince, M (2010). World Alzheimer Report 2010: The Global Economic Impact of Dementia. Alzheimer's Disease International.
10. Taylor, J P, Hardy, J and Fischbeck, K H (2002). Toxic proteins in neurodegenerative disease. Science 296: 1991-1995.
11. Mattson, M P (2004). Pathways towards and away from Alzheimer's disease. Nature 430: 631-639.
12. Tabaton, M and Tamagno, E (2007). The molecular link between beta- and gamma-secretase activity on the amyloid beta precursor protein. Cell Mol Life Sci 64: 2211-2218.
13. Tsai, J, Grutzendler, J, Duff, K and Gan, W B (2004). Fibrillar amyloid deposition leads to local synaptic abnormalities and breakage of neuronal branches. Nat Neurosci 7: 1181-1183.
14. Farlow, M R, Salloway, S, Tariot, P N, Yardley, J, Moline, M L, Wang, Q et al. (2010). Effectiveness and tolerability of high-dose (23 mg/d) versus standard-dose (10 mg/d) donepezil in moderate to severe Alzheimer's disease: A 24-week, randomized, double-blind study. Clin Ther 32: 1234-1251.
15. Guo, L, Duggan, J and Cordeiro, M F (2010). Alzheimer's disease and retinal neurodegeneration. Curr Alzheimer Res 7: 3-14.
16. Lee, A G and Martin, C O (2004). Neuro-ophthalmic findings in the visual variant of Alzheimer's disease. Ophthalmology 111: 376-380.
17. Janciauskiene, S and Krakau, T (2003). Alzheimer's peptide and serine proteinase inhibitors in glaucoma and exfoliation syndrome. Doc Ophthalmol 106: 215-223.
18. Janciauskiene, S and Krakau, T (2001) Alzheimer's peptide: a possible link between glaucoma, exfoliation syndrome and Alzheimer's disease. Acta Ophthalmol Scand 79: 328-329.
19. Yoshida, T, Ohno-Matsui, K, Ichinose, S, Sato, T, Iwata, N, Saido, T C et al. (2005). The potential role of amyloid beta in the pathogenesis of age-related macular degeneration. J Cli Invest 115: 2793-2800.
20. Goldstein, L E, Muffat, J A, Cherny, R A, Moir, R D, Ericsson, M H, Huang, X et al. (2003). Cytosolic beta-amyloid deposition and supranuclear cataracts in lenses from people with Alzheimer's disease. Lancet 361: 1258-1265.
21. Guo, L, Salt, T E, Luong, V, Wood, N, Cheung, N, Maass, A et al. (2007). Targeting amyloid-beta in glaucoma treatment. Proc Natl Acad Sci USA 104: 13444-13449.
22. Zimran, A, Brill-Almon, E, Chertkoff, R, Petakov, M, Blanco-Favela, F, Munoz, E T et al. (2011). Pivotal trial with plant-cell-expressed recombinant glucocerebrosidase, taliglucerase alfa, a novel enzyme replacement therapy for Gaucher disease. Blood 118: 5767-5773.
23. Kwon, K C, Verma, D, Singh, N D, Herzog, R and Daniell, H (2013). Oral delivery of human biopharmaceuticals, autoantigens and vaccine antigens bioencapsulated in plant cells. Adv Drug Deliver Rev 65: 782-799.
24. Limaye, A, Koya, V, Samsam, M and Daniell, H (2006). Receptor-mediated oral delivery of a bioencapsulated green fluorescent protein expressed in transgenic chloroplasts into the mouse circulatory system. FASEB J 20: 959-961.
25. Boggs, J M (2006). Myelin basic protein: a multifunctional protein. Cell Mol Life Sci 63: 1945-1961.
26. Mitew, S, Kirkcaldie, M T, Halliday, J M, Shepherd, C E, Vickers, J C and Dickson, T C (2010). Focal demyelination in Alzheimer's disease and transgenic mouse models. Acta Neuropathol 119: 567-577.
27. Liao, M C, Hoos, M D, Aucoin, D, Ahmed, M, Davis, J Smith, S O et al. (2010). N-terminal domain of myelin basic protein inhibits amyloid beta-protein fibril assembly. J Biol Chem 285: 35590-35598.
28. Hoos, M D, Ahmed, M, Smith, S O and Van Nostrand, W E (2009). Myelin basic protein binds to and inhibits the fibrillar assembly of Abeta42 in vitro. Biochemistry 48: 4720-4727.
29. Ruhlman, T, Verma, D, Samson, N and Daniell, H (2010). The Role of Heterologous Chloroplast Sequence Elements in Transgene Integration and Expression. Plant Physiol 152: 2088-2104.
30. Verma, D, Samson, N P, Koya, V and Daniell, H (2008). A protocol for expression of foreign genes in chloroplasts. Nat Protoc 3: 739-758.
31. Fang, Y, Xie, X, Ledeen, R W and Wu, G (2002). Characterization of cholera toxin B subunit-induced Ca2+ influx in neuroblastoma cells: evidence for a voltage-independent GM1 ganglioside-associated Ca2+ channel. J Neurosci Res 69: 669-680.

32. Masters, C L and Selkoe, D J (2012). Biochemistry of amyloid-β and amyloid deposits in Alzheimer's disease. Cold Spring Harb Perspect Med doi: 10.1101/cshperspect.a006262.
33. Sanchez, J and Holmgren, J (2008). Cholera toxin structure, gene regulation and pathophysiological and immunological aspects. Cell Mol. Life Sci. 65, 1347-1360.
34. Georgieva, J V (2012). Peptide-mediated blood-brain barrier transport of polymersomes. Angew Chem Int Edit. 51:8339-8342.
35. Bowman, G L, Kaye, J A, Moore, M, Waichunas, D, Carlson, N E and Quinn J F (2007). Blood-brain barrier impairment in Alzheimer disease: stability and functional significance. Neurology 68: 1809-1814.
36. Liao, M C, Ahmed, M, Smith, S O and Van Nostrand, W E (2007). Degradation of amyloid β protein by purified myelin basic protein. J Biol Chem 284: 28971-28925.
37. Urbanc, B, Cruz, L, Le, R, Sanders, J, Hsiao-Ashe, K, Duff, K et al. (2002). Neurotoxic effects of thioflavin S positive amyloid deposits in transgenic mice and Alzheimer's disease. Proc. Natl. Acad. Sci USA 99: 13990-13995.
38. Reilly, J F, Games, D, Ryde, R E, Freedman, S, Schenk, D, Young, W G et al. (2003). Amyloid deposition in the hippocampus and entorhinal cortex: quantitative analysis of a transgenic mouse model. Pro. Natl Acad Sci USA 100: 4837-4842.
39. Parihar, M S and Brewer, G J (2010). Amyloid Beta as a Modulator of Synaptic Plasticity. J Alzheimers Dis 22: 741-763.
40. Yotteri, R A, Doshi, J, Clark, V, Sojkova, J, Zhou, Y, Wong, D F et al. (2013). Memory decline shows stronger associations with estimated spatial patterns of amyloid deposition progression than total amyloid burden. Neurobiol Aging doi: 10.1016/j.neurobiolaging.2013.05.030.
41. Fu, H J, Liu, B, Frost, J L and Lemere, C A (2010). Amyloid-β immunotherapy for Alzheimer's disease. CNS Neurol Disord Drug Targets 9: 197-206.
42. Lee, S B, Li, B, Jin, S and Daniell, H (2011). Expression and characterization of antimicrobial peptides retrocyclin 101 and protegrin-1 in chloroplasts to control viral and bacterial infections. Plant Biotechnol J 9: 100-115.
43. Kwon, K C, Nityanandam, R, New, J S and Daniell, H (2013). Oral delivery of bioencapsulated exendin-4 expressed in chloroplasts lowers blood glucose level in mice and stimulates insulin secretion in beta-TC6 cells. Plant Biotechnol J 11: 77-86.
44. Lakshmi, P S, Verma, D, Yang, X, Lloyd, B and Daniell, H (2013). Low Cost Tuberculosis Vaccine Antigens in capsules: Expression in Chloroplasts, Bio-encapsulation, Stability and Functional Evaluation in vitro. PLoS One 8: e54708
45. Hill, D R, Ford, L and Lalloo, D G (2006). Oral cholera vaccines: use in clinical practice. Lancet Infect. Dis. 6, 361-73.
46. Wang, X M, Sherman, A, Liao, G, Leong, K W, Daniell H, Terhorst, C et al. (2013). Mechanism of oral tolerance induction to therapeutic proteins. Adv. Drug Deliv. Rev. 65: 759-773.
47. Verma, D, Moghimi, B, LoDuca, P A, Singh, H D, Hoffman, B E, Herzog, R W et al. (2010). Oral delivery of bioencapsulated coagulation factor IX prevents inhibitor formation and fatal anaphylaxis in hemophilia B mice. Proc Natl Acad Sci USA 107: 7101-7106.
48. Ruhlman, T, Ahangari, R, Devine, A, Samsam, M and Daniell, H (2007). Expression of cholera toxin B-proinsulin fusion protein in lettuce and tobacco chloroplasts—oral administration protects against development of insulitis in non-obese diabetic mice. Plant Biotechnol J 5: 495-510.
49. Chigurupati, S, Madan, M, Okun, E, Wei, Z, Pattisapu, J V, Mughal, M R et al. (2011). Evidence for altered numb isoform levels in Alzheimer Disease patients and a triple transgenic mouse model. J Alzheimers Dis 24: 349-361.

While certain of the preferred embodiments of the present invention have been, described and specifically exemplified above, it is not intended that the invention be limited to such embodiments. Various modifications may be made thereto without departing from the scope and spirit of the present invention, as set forth in the following claims.

What is claimed is:

1. A method for delivery of human myelin basic protein (MBP) across the blood brain barrier and blood retinal barrier in a subject in need thereof, said subject having a central nervous system disorder, comprising:
    a) administering to the subject a composition comprising lyophilized leaf material containing an effective amount of a fusion protein comprising said MBP operably linked to cholera toxin B (CTB) subunit in a 1:1 ratio under conditions whereby said fusion protein crosses the blood brain and blood retinal barrier and wherein said composition is administered orally and effective to
        i) reduce levels of amyloid beta protein in the brain; and/or
        ii) reduce amyloid levels in the retina; and/or
        iii) prevent loss of retinal ganglion cells; and/or
        iv) decrease the ratio of insoluble vs soluble amyloid beta protein42 in hippocampus;
    said CTB-MBP fusion protein being present in a plastid transformed with a stable plastid transformation vector and expression vector which expresses said CTB-MBP fusion protein in said leaf material, wherein said CTB and human MBP are separated by a glycine-proline-glycine-proline hinge region and a furin site,
    wherein the subject is assessed for the reduction of amyloid plaque levels.

2. The method of claim 1, wherein said subject is a human or nonhuman mammal.

* * * * *